United States Patent [19]
Fallon et al.

[11] Patent Number: 5,888,785
[45] Date of Patent: Mar. 30, 1999

[54] METHOD FOR USING HYDRATASE OR A HYDRATASE-AMIDASE FUSION FOR STEREOSPECIFICALLY BIOCONVERTING CERTAIN RACEMIC NITRILES TO THE CORRESPONDING ENATIOMERIC R—OR S-AMIDE OR S-CARBOXYLIC ACID

[75] Inventors: Robert Donald Fallon, Elkton, Md.; Mark James Nelson, Newark; Mark Scott Payne, Wilmington, both of Del.

[73] Assignee: E. I. du Pont de Nemours and Company, Wilmington, Del.

[21] Appl. No.: 103,411

[22] Filed: Jun. 24, 1998

Related U.S. Application Data

[62] Division of Ser. No. 726,136, Oct. 4, 1996, Pat. No. 5,811,286.

[60] Provisional application No. 60/004,914 Oct. 6, 1995.

[51] Int. Cl.⁶ .............................. C12P 13/02; C12P 7/40; C12N 9/80; C12N 9/88
[52] U.S. Cl. ........................... 435/129; 435/41; 435/136; 435/228; 435/232; 435/252.3; 435/877
[58] Field of Search .................................... 435/129, 136, 435/41, 228, 232, 252.3, 877

[56] References Cited

U.S. PATENT DOCUMENTS

| | | | |
|---|---|---|---|
| 4,366,250 | 12/1982 | Jallageas et al. | 435/280 |
| 5,034,329 | 7/1991 | Cerbelaud et al. | 435/280 |
| 5,238,828 | 8/1993 | Murakami | 435/136 |
| 5,314,819 | 5/1994 | Morimoto et al. | 435/232 |

FOREIGN PATENT DOCUMENTS

| | | |
|---|---|---|
| 2 010 929 | 12/1990 | Canada . |
| 433 117 A | 6/1991 | European Pat. Off. . |
| 445 646 A | 9/1991 | European Pat. Off. . |
| 0 502 476 | 9/1992 | European Pat. Off. . |
| 05-252990 A | 3/1992 | Japan . |
| 06 303 971 A | 1/1994 | Japan . |
| WO 86/07386 | 12/1986 | WIPO . |
| WO 92/05275 | 4/1992 | WIPO . |
| WO 95/04828 | 2/1995 | WIPO . |

OTHER PUBLICATIONS

Azza, S. et al, "Cloning of the wide spectrum amidase gene from Brevibacterium sp. R312 by genetic complementation. Overexpression in Brevibacterium sp. and *Escherichia coli*", *FEMS Microbiol. Lett.*, 122, 129–136 (1994).

Kobayashi, M. et al, "Amidase coupled with low–molecular–mass nitrile hydratase from Rhodococcus rhodochrous J1", *Eur. J. Biochem.*, 217, 327–336 (1993).

Blakey, A.J. et al, "Regio–and stereo–specific nitrile hydrolysis by the nitrile hydratase from Rhodococcus AJ270", *FEMS Microbiology Lett.*, 129, 57–62 (1995).

Ikehata, O. et al, "Primary structure of nitrile hydratase deduced from the nucleotide sequence of a Rhodococcus species and its expression in *Escherichia coli*", *Eur. J. Biochem.*, 181, 563–570 (1989).

Nishiyama, M. et al, "Cloning and Characterization of Genes Responsible for Metabolism of Nitrile Compounds from *Pseudomonas chloroaphis* B23", *J. of Bacteriology*, 173(8), 2465–2472 (1991).

Kobayashi, M. et al, "Cloning, nucleotide sequence and expression in *Escherichia coli* of two cobalt–containing nitrile hydratase genes", *Biochimica et Biophysica Acta.*, 1129, 23–33 (1991).

Mayaux, J. et al, "Purification, Cloning, and Primary Structure of an Enantiomer–Selective Amidase from Brevibacterium sp. Strain R312: Structural Evidence for Genetic Coupling with Nitrile Hydratase"., *J. Bacteriol.*, 172(12), 6764–6773 (1990).

*Primary Examiner*—Robert A. Wax
*Assistant Examiner*—Elizabeth Slobodyansky

[57] ABSTRACT

The present invention provides a nitrile hydratase nucleic acid fragment isolated from *Pseudomonas putida* which encodes a nitrile hydratase activity capable of catalyzing the hydrolysis of certain racemic nitrites to the corresponding R- or S-amides. Also provided are transformed microorganisms capable of the active expression of said nitrile hydratase activity. Additionally, the invention provides a transformant harboring the nitrile hydratase gene in conjunction with an amidase gene, both of which may be co-expressed producing active nitrile hydratase and amidase enzymes respectively. Methods for the production of such enantiomeric materials are also provided.

4 Claims, 10 Drawing Sheets

FIG. 7

SEQ ID NO:17:

| | | | | | | |
|---|---|---|---|---|---|---|
| CGGGAGCGCA | ATCTGCAAGG | TGGCATTGGC | CTTCAGTGTC | GATGCCGAGT | TGAAGTCGCT | 60 |
| GTACCCCTTT | TTTCAACCAC | ACCAGGAGAA | CCGCACCATG | GGCAATCAC | ACACGCATGA | 120 |
| CCACCATCAC | GACGGGTACC | AGGCACCGCC | CGAAGACATC | GCGCTGCGGG | TCAAGGCCTT | 180 |
| GGAGTCTCTG | CTGATCGAGA | AAGGTCTTGT | CGACCCAGCG | GCCATGGACT | TGGTCGTCCA | 240 |
| AACGTATGAA | CACAAGGTAG | GCCCCCGAAA | CGGCGCCAAA | GTCGTGGCCA | AGGCCTGGGT | 300 |
| GGACCCTGCC | TACAAGGCCC | GTCTGCTGGC | AGACGCAACT | GCGGCAATTG | CCGAGCTGGG | 360 |
| CTTCTCCGGG | GTACAGGGCG | AGGACATGGT | CATTCTGGAA | AACACCCCCG | CCGTCCACAA | 420 |
| CGTCTTCGTT | TGCACCTTGT | GCTCTTGCTA | CCCATGGCCG | ACGCTGGGCT | TGCCCCCTGC | 480 |
| CTGGTACAAG | GCCGCCGCCT | ACCGGTCCCG | CATGGTGAGC | GACCCGCGTG | GGGTTCTCGC | 540 |
| GGAGTTCGGC | CTGGTGATCC | CCGCCAACAA | GGAAATCCGC | GTCTGGGACA | CCACGGCCGA | 600 |
| ATTGCGCTAC | ATGGTGCTGC | CGGAACGGCC | CGGAACTGAA | GCCTACAGCG | AAGAACAACT | 660 |
| GGCCGAACTC | GTTACCCGCG | ATTCGATGAT | CGGCACCGGC | CTGCCAACCC | AACCCACCCC | 720 |
| ATCTCATTAA | GGAGTTCGTC | ATGAATGGCA | TTCACGATAC | TGGCGGAGCA | CATGGTTATG | 780 |
| GGCCGGTTTA | CAGAGAACCG | AACGAACCCG | TCTTTCGCTA | CGACTGGGAA | AAAACGGTCA | 840 |
| TGTCCCTGCT | CCCGGCCCTG | CTCGCCAACG | CGAACTTCAA | CCTCGATGAA | TTTCGGCATT | 900 |
| CGATCGAGCG | AATGGGCCCG | GCCCACTATC | TGGAGGGAAC | CTACTACGAA | CACTGGCTTC | 960 |
| ATGTCTTTGA | GAACCTGCTG | GTCGAGAAGG | GTGTGCTCAC | GGCCACGGAA | GTCGCGACCG | 1020 |
| GCAAGGCTGC | GTCTGGCAAG | ACGGCGACGC | GCGTGCTGAC | GCCGGCCATC | GTGGACGACT | 1080 |
| CGTCAGCACC | GGGGCTTCTG | CGCCCGGGAG | GAGGGTTCTC | TTTTTTTCCT | GTGGGGGACA | 1140 |
| AGGTTCGCGT | CCTCAACAAG | AACCCGGTGG | CCATACCCG | CATGCCGCGC | TACACGCGGG | 1200 |
| CAAAGTGGGG | ACAGTGGTCA | TCGACCATGG | TGTGTTTCGT | GACGCCGGAC | ACCGCGGCAC | 1260 |
| ACGGAAAGGG | CGAGCAGCCC | CAGCACGTTT | ACACCGTGAG | TTTCACGTCG | GTCGAACTGT | 1320 |
| GGGGGCAAGA | CGCTTCCTCG | CCGAAGGACA | CGATTCGCGT | CGACTTGTGG | GATGACTACC | 1380 |
| TGGAGCCAGC | GTGATCATGA | AAGACGAACG | GTTTCCATTG | CCAGAGGGTT | CGCTGAAGGA | 1440 |

METHOD FOR USING HYDRATASE OR A HYDRATASE-AMIDASE FUSION FOR STEREOSPECIFICALLY BIOCONVERTING CERTAIN RACEMIC NITRILES TO THE CORRESPONDING ENATIOMERIC R— OR S-AMIDE OR S-CARBOXYLIC ACID

This is a division of application Ser. No. 08/726,136 filed Oct. 4, 1996, now U.S. Pat. No. 5,811,286, claiming benefit of P1 case 60/004,914 filed Oct. 6, 1995.

FIELD OF INVENTION

The present invention relates to the field of molecular biology and methods for the isolation and expression of foreign genes in recombinant microorganisms. More specifically, the invention relates to the isolation, sequencing, and recombinant expression of nucleic acid fragments (genes) encoding a stereospecific, nitrile hydratase (NHase) activity capable of catalyzing the hydrolysis of certain racemic nitrites to the corresponding R- or S- amides. Additionally, the invention relates to the co-expression of the nitrile hydratase nucleic acid fragment with a nucleic acid fragment encoding a stereospecific amidase activity capable of converting a racemic mixture of R- and S- amides to the corresponding enantiomeric R- or S- carboxylic acids.

BACKGROUND

Many agrochemicals and pharmaceuticals of the general formula X—CHR—COOH are currently marketed as racemic or diastereomer mixtures. In many cases the physiological effect derives from only one enantiomer/diastereomer where the other enantiomer/diastereomer is inactive or even harmful. Methods for synthesizing enantiomers are becoming increasingly important tools for the production of chemicals of enantiomer purity. To date, however, no recombinant, stereospecific NHase has been described capable of catalyzing the hydrolysis of certain racemic nitriles to the corresponding R- or S- amides.

Methods for the selective preparation of stereospecific amides from nitrites are known and incorporate microorganisms possessing nitrile hydratase activity (NHase). These NHases catalyze the addition of one molecule of water to the nitrile, resulting in the formation of the amide free product according to Reaction 1:
Reaction 1

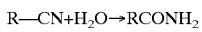

Similarly, methods for the stereospecific production of carboxylic acids are known and incorporate microorganisms possessing an amidase (Am) activity. In general amidases convert the amide product of Reaction 1 to the acid free product plus ammonia according to Reaction 2:
Reaction 2

A wide variety of bacterial genera are known to possess a diverse spectrum of nitrile hydratase and amidase activities including Rhodococcus, Pseudomonas, Alcaligenes, Arthrobacter, Bacillus, Bacteridium, Brevibacterium, Corynebacterium, and Micrococcus. For example, nitrile hydratase enzymes have been isolated from *Pseudomonas chlororaphis*, B23 [Nishiyama, M. J., *Bacteriol.*, 173:2465–2472 (1991)] *Rhodococcus rhodochrous* J1 [Kobayashi, M., *Biochem. Biophys. Acta*, 1129:23–33 (1991)] *Brevibacterium* sp. 312(Mayaux et al.,*J. Bacteriol.*, 172:6764–6773 (1990)), and *Rhodococcus* sp. N-774 [Ikehata, O., Nishiyama, M., Horinouchi, S., Beppu, T.,*Eur. J. Biochem.*, 181: 563–570(1989)]. No disclosure of any stereoselective activity is made for any of these enzymes. Only two disclosures have been made for stereoselective nitrile hydratase activity in native bacterial strains. The Applicants have disclosed a stereospecific nitrile hydratase from P. putida NRRL-18668 [WO 92/05275 (1990)].

Wildtype microorganisms known to possess nitrile hydratase activity have been used to convert nitrites to amides and carboxylic acids. For example, EPA 326,482 discloses the stereospecific preparation of aryl-2-alkanoic acids such as 2-(4-chlorophenyl)-3 -methylbutyric acid by microbial hydrolysis of the corresponding racemic amide using members of Brevibacterium and Corynebacterium. Similarly, U.S. Pat. No. 4,366,250 teaches the use of Bacillus, Bacteridium, Micrococcus and Brevibacterium in a method for the preparation of L-amino acids from the corresponding racemic amino nitriles. Finally, WO 92/05275 teaches a biologically-catalyzed method for converting a racemic alkyl nitrile to the corresponding R- or S-alkanoic acid through an intermediate amide using members of the bacterial genera *Pseudomonas* spp. (e.g., *putida, aureofaciens, Moraxella* spp.) and Serratia (e.g., *Serratia liquefaciens*).

In addition to the use of wildtype organisms, recombinant organisms containing heterologous genes for the expression of nitrile hydratase are also known for the conversion of nitrites. For example, Cerebelaud et al., (WO 9504828) teach the isolation and expression in *E. coli* of nitrile hydratase genes isolated from *C. testosteroni*. The transformed hosts effectively convert nitrites to amides where the nitrile substrate consists of one nitrile and one carboxylate group. However, WO 9504828 does not teach a stereospecific conversion of nitrites.

Similarly, Beppu et al., (EP 5024576) disclose plasmids carrying both nitrile hydratase and amidase genes from Rhodococcus capable of transforming *E. coli* where the transformed host is then able to use isobutyronitrile and isobutyroamide as enzymatic substrates. However, EP 5024576 does not teach a stereospecific conversion of nitrites or amides.

As with nitrile hydratases, microorganisms possessing amidase activity have been used to convert amides to carboxylic acids. In U.S. Ser. No. 08/403911, Applicants disclose a method for converting an (S)-amide, or stereospecifically converting a mixture of (R)- and (S)-amides to the corresponding enantiomeric (S)-carboxylic acid by contacting said amide with *Pseudomonas chlororaphis* B23 in a solvent. This method uses a wildtype microorganism and does not anticipate a recombinant catalyst or heterologous gene expression. Blakey et al., *FEMS Microbiology Letters*, 129:57–62 (1995) disclose a *Rhodococcus* sp. having activity against a broad range of nitrites and dinitriles and able to catalyze regio-specific and stereo-specific nitrile biotransformations.

Genes encoding amidase activity have been cloned, sequenced, and expressed in recombinant organisms. For example, Azza et al., (*FEMS Microbiol. Lett.* 122, 129, (1994)) disclose the cloning and over-expression in *E. coli* of an amidase gene from *Brevibacterium* sp. R312 under the control of the native promoter. Similarly, Kobayashi et al., (*Eur. J. Biochem.*, 217, 327, (1993)) teach the cloning of both a nitrile hydratase and amidase gene from *R. rhodococcus* J1 and their co-expression in *E. coli*.

What is needed and inventive over the prior art is a method for the stereospecific conversion of racemic alkyl nitriles to the corresponding R- or S-alkanoic acids using a recombinant organism.

SUMMARY OF THE INVENTION

This invention relates to nucleic acid fragments encoding:
1) the α subunit of a stereospecific nitrile hydratase enzyme, said gene having at least a 64% base homology with the α subunit coding region of the *Rhodococcus rhodochrous* J1 L-NHase gene [Kobayashi, M., Biochem. Biophys. Acta, 1129:23–33 (1991)] and said enzyme capable of catalyzing the hydrolysis of racemic aryl-2-alkane nitrites to the corresponding R- or S- amides; and
2) the β subunit of a stereospecific nitrile hydratase enzyme, said gene having at least a 52% base homology with the β subunit coding region of the *Rhodococcus rhodochrous* J1 L-NHase gene and said enzyme capable of catalyzing the hydrolysis of racemic aryl-2-alkane nitrites to the corresponding R- or S-amides.

Another embodiment of the invention is a nucleic acid fragment comprising the nucleic acid fragments encoding both the α and β subunits of a stereospecific nitrile hydratase enzyme described above, said enzyme capable of catalyzing the hydrolysis of racemic aryl-2-alkane nitrites to the corresponding R- or S-amides.

A further embodiment of the invention is a nucleic acid fragment encoding the α subunit of a stereospecific nitrile hydratase enzyme, said nucleic acid fragment having the nucleotide sequence as represented in SEQ ID NO.:3 and said enzyme capable of catalyzing the hydrolysis of racemic alkyl nitrites to the corresponding R- or S- amides.

A further embodiment of the invention is a nucleic acid fragment encoding the β subunit of a stereospecific nitrile hydratase enzyme, said nucleic acid fragment having the nucleotide sequence as represented in SEQ ID NO.:4 and said enzyme capable of catalyzing the hydrolysis of racemic alkyl nitrites to the corresponding R- or S- amides.

Still another embodiment of the invention is a nucleic acid fragment encoding both the α and β subunits of a stereospecific nitrile hydratase enzyme, said nucleic acid fragment having the nucleotide sequence as represented in SEQ ID NO.:17 and said enzyme capable of catalyzing the hydrolysis of racemic aryl-2-alkane nitrites to the corresponding R- or S- amides.

Further embodiments of the invention include
1) the polypeptide a subunit of a stereospecific nitrile hydratase enzyme, said α subunit having the amino acid sequence as represented in SEQ ID NO.:1 and said enzyme being capable of catalyzing the hydrolysis of racemic aryl-2-alkane nitrites to the corresponding R- or S- amides; and
2) the polypeptide β subunit of a stereospecific nitrile hydratase enzyme, said β subunit having the amino acid sequence as represented in SEQ ID NO.:2 and said enzyme being capable of catalyzing the hydrolysis of racemic aryl-2-alkane nitrites to the corresponding R- or S- amides.

A further embodiment of the invention is a stereospecific nitrile hydratase enzyme, said enzyme comprising the combined α and β subunits having the respective amino acid sequences SEQ ID NOs.:1 and 2 in proper conformation such that said enzyme catalyzes the hydrolysis of racemic aryl-2-alkane nitrites to the corresponding R- or S- amides.

A still further embodiment of the invention is a 6.5 kb nucleic acid fragment encoding a nitrile hydratase enzyme and the accessory nucleic acid fragments necessary for the enzymes's active expression and further characterized by the restriction fragment map shown in FIG. 2. This 6.5 kb nucleic acid fragment is incorporated into an expression vector capable of transforming a suitable host cell for the expression of active stereospecific nitrile hydratase as characterized by the plasmid map shown in FIG. 3.

The invention further provides a region of the *P. putida* genome encompassed within the 6.5 kb fragment, designated P14K, which encodes a polypeptide that is necessary for the bioactivity of the stereospecific nitrile hydratase enzyme isolated from *Pseudomonas putida* NRRL-18668.

Additionally the invention provides a nucleic acid fragment encoding a 18668 amidase having an amino acid sequence as represented in SEQ ID NO.:28, wherein the amino acid sequence may encompass amino acid substitutions, deletions or additions that do not alter the function of said amidase. The 18668 amidase is isolated from *Pseudomonas putida* NRRL-18668 and is distinct from the amidase isolated from *Pseudomonas chlororaphis* B-23 (FERM B-187).

The present invention further provides recombinant hosts, transformed with the nucleic acid fragment encoding a 18668 amidase and/or the genes encoding the α, β nitrile hydratase subunits and the P14K region of the *Pseudomonas putida* NRRL-18668 genome.

The invention also provides methods for the conversion of racemic nitrites to the corresponding R- or S-amides or corresponding enantiomeric R- or S-carboxylic acids using the above transformed hosts containing nucleic acid fragments encoding a 18668 amidase and/or the genes encoding the α, β nitrile hydratase subunits and the P14K region of the *Pseudomonas putida* NRRL-18668 genome.

Other embodiments of the invention are:
1) a transformed microbial host cell comprising the nucleic acid fragment represented by SEQ ID NO.:17 wherein said host cell expresses active nitrile hydratase enzyme capable of catalyzing the hydrolysis of racemic aryl-2 alkane nitriles to the corresponding R- or S- amides; and
2) a transformed microbial host cell comprising the 6.5 kb nucleic acid fragment characterized by the restriction map shown in FIG. 2 wherein said host cell expresses active nitrile hydratase enzyme capable of catalyzing the hydrolysis of racemic aryl-2 alkane nitriles to the corresponding R- or S- amides.

Other embodiments of the invention are host cells transformed with nucleic acid fragments represented by SEQ ID NO.:17 or the restriction maps of FIGS. 2 and 3, wherein the host cell is selected from the group consisting of bacteria of the genera Escherichia, Pseudomonas, Rhodococcus, Acinetobacter, Bacillus, and Streptomyces, yeast of the genera Pichia, Hansenula, and Saccharomyces, and filamentous fungi of the genera Aspergillus, Neurospora, and Penicillium.

A particular embodiment of the invention is *Escherichia coli* transformed with the nucleic acid fragment represented by SEQ ID NO.:17 or the nucleic acid fragment represented by the restriction map of FIG. 2.

A further embodiment of the invention is an expression vector described in FIG. 6 comprising 1) a 5.0 kb nucleic acid fragment from the 6.5 kb fragment of claim 10, and 2) a nucleic acid fragment having the nucleic acid sequence as given in SEQ ID NO.:20, wherein said nucleic acid fragment encodes an amidase enzyme, and wherein said expression vector is capable of transforming suitable host cells for the co-expression of active stereospecific nitrile hydratase and amidase. A further embodiment is a host cell transformed with this expression vector wherein more particularly the host is selected from the group consisting of the genera Escherichia, Pseudomonas, Rhodococcus, Acinetobacter, Bacillus, Streptomyces, Hansenula, Saccharomyces, Pichia, Aspergillus, Neurospora, and Penicillium. A further embodiment is *Escherichia coli* SW17 transformed with pSW17.

A further embodiment of the invention is a method for converting a nitrile of the formula

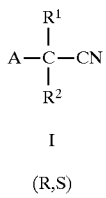

(R,S)

wherein:

A is selected from the group consisting of:

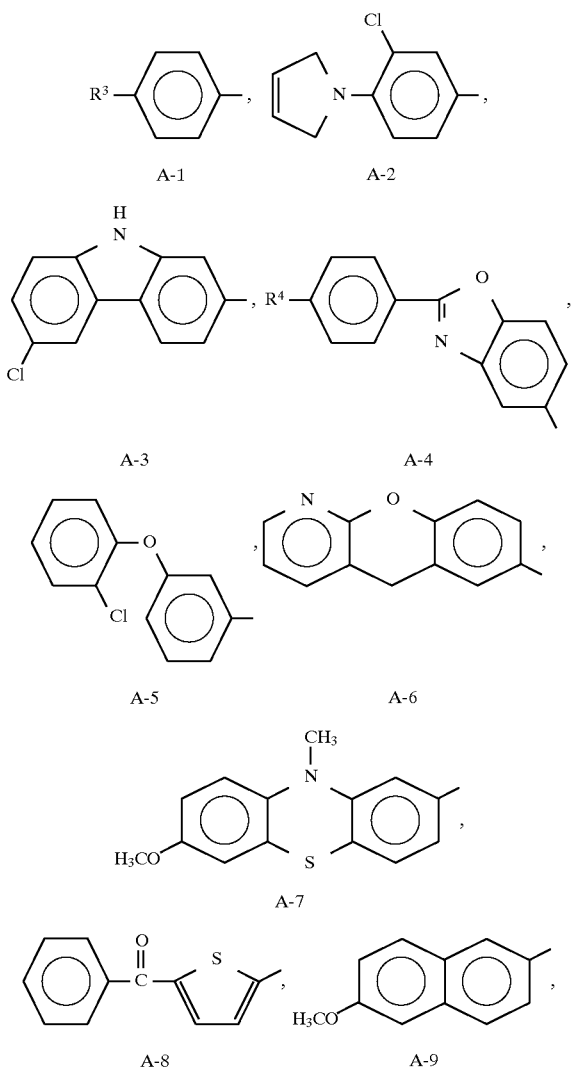

-continued

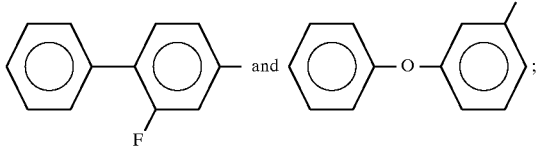

$R^1$ is $C_1$–$C_4$ alkyl;
$R^2$ is H or OH;
$R^3$ is H, Cl, OCF$_3$H, (CH$_3$)$_2$CHCH$_2$, H$_2$C=C(CH$_3$)CH$_2$NH,

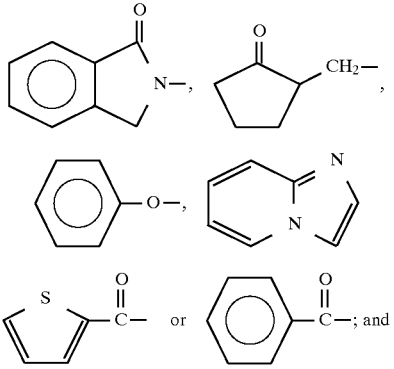

$R^4$ is Cl or F;

to the corresponding amide comprising contacting said nitrile with the transformed host cell containing a nucleic acid fragment having the nucleotide sequence represented by SEQ ID NO.:17 that stereospecifically converts the racemic nitrile to the corresponding enantiomeric R- or S-amide, the host cell selected from the group consisting of Escherichia, Pseudomonas, Rhodococcus, Acinetobacter, Bacillus, Streptomyces, Hansenula, Saccharomyces, Pichia, Aspergillus, Neurospora, and Penicillium.

The Applicants also provide a method for the conversion of the above described nitrile to corresponding enantiomeric (R) or (S)-carboxylic acid by contacting the nitrile with the transformed host comprising an expression vector comprising a nucleic acid fragment represented by FIG. 2 and the nucleic acid sequence of SEQ ID NO.:20, the host cell selected from the group consisting of Escherichia, Pseudomonas, Rhodococcus, Acinetobacter, Bacillus, Streptomyces, Hansenula, Saccharomyces, Pichia, Aspergillus, Neurospora, and Penicillium.

A further embodiment of the invention is a nucleic acid fragment encoding the α and β subunits of a stereospecific nitrile hydratase enzyme, said portion of the nucleic acid fragment encoding the α subunit having at least a 64% base homology to the Rhodochrous J1 L-NHase gene and said portion of the nucleic acid fragment encoding the β subunit having a 52% base homology to the Rhodochrous J1 L-NHase gene, and said enzyme capable of catalyzing the hydrolysis of racemic aryl-2-alkane nitrites to the corresponding R- or S- amides.

Yet another embodiment of the invention is the polypeptide encoded by any one of the nucleic acid fragments of the invention.

Embodiments of the invention are plasmids pSW2 carried in SW2 and designated as ATCC 69888, pSW17 carried in SW17 and designated as ATCC 69887, pSW50 carried in *P. pastoris* SW50.2 and designated as ATCC 74391, pSW37 carried in *E. coli* SW37 and designated as ATCC 98174, and pSW23 carried in *E. coli* SW23 and designated as ATCC 98175.

BRIEF DESCRIPTION OF THE FIGURES BIOLOGICAL DEPOSITS AND SEQUENCE LISTING

Figure 5:
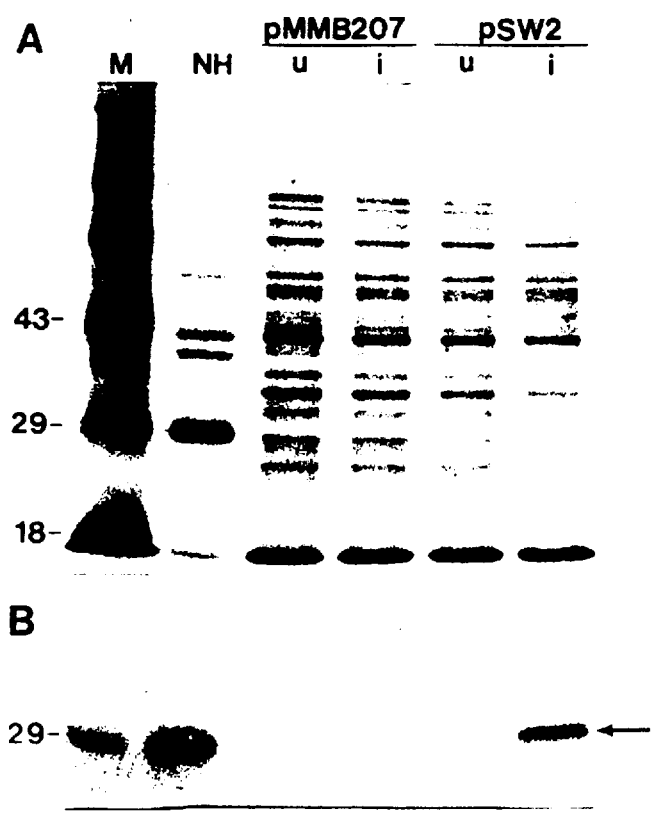

FIG. 5 is a western blot analysis showing the production of NRRL-18668 nitrile hydratase protein in *E. coli*. (A) Coomassie Blue stained SDS-PAGE gel of protein extracts from uninduced (u) and induced (i) *E. coli* transformed with the plasmid pSW2. (B) Western blot analysis of duplicate gel shown in (A) using anti-NH sera. M, protein molecular weight markers; NH, nitrile hydratase protein from NRRL-18668. Arrow indicates NH.

Figure 6:
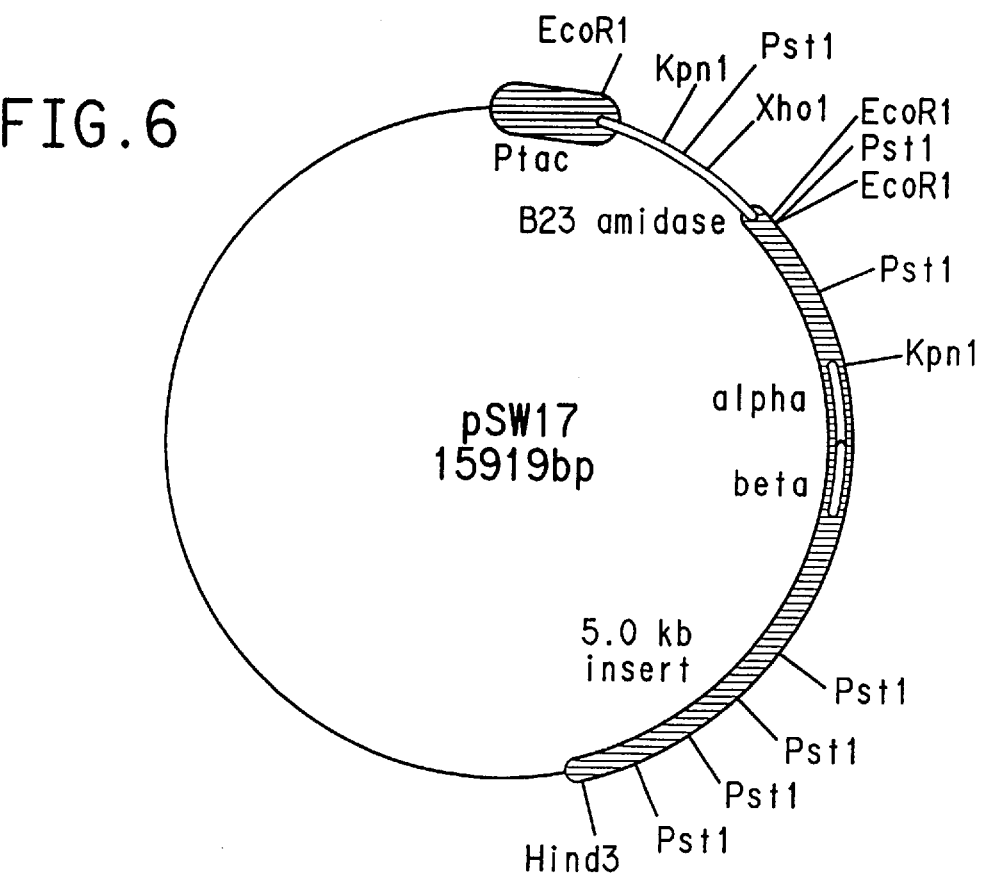

FIG. 6 is a plasmid map of the plasmid pSW17 created by inserting a 1.5 kb DNA fragment comprising the gene encoding amidase from *Pseudomonas chlororaphis* B23, and a 5.0 kb subclone of the 6.5 kb DNA fragment comprising the genes encoding the α and β subunits of nitrile hydratase into the wide-host-range vector pMMB207.

FIG. 7 illustrates the nucleotide and amino acid sequences of the *Pseudomonas putida* (NRRL-18668) α and β nitrile hydratase coding regions also found in SEQ ID NO.:17.

Figure 8:
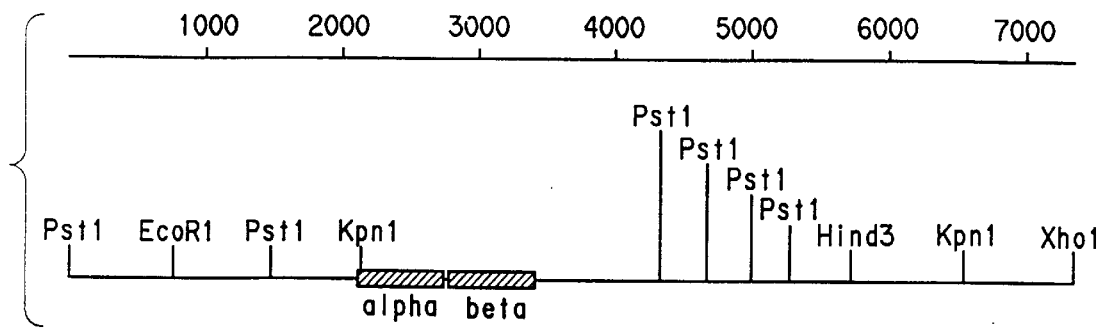

FIG. 8 is a restriction map of the 6.5 kb nucleic acid fragment which includes the nitrile hydratase gene isolated from *P. putida* (NRRL-18668) plus sequence upstream of the EcoR1 site (shown in FIG. 2) including a new Pst1 site.

Figure 9:
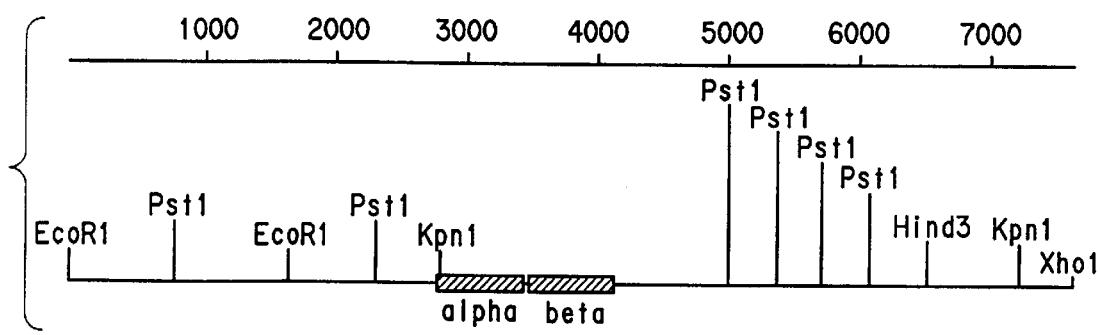

FIG. 9 is a restriction map of the 6.5 kb nucleic acid fragment which includes the nitrile hydratase gene isolated from *P. putida* (NRRL-18668) plus sequence upstream of the new Pst1 site (shown in FIG. 8) including a new EcoR1 site.

Figure 10:
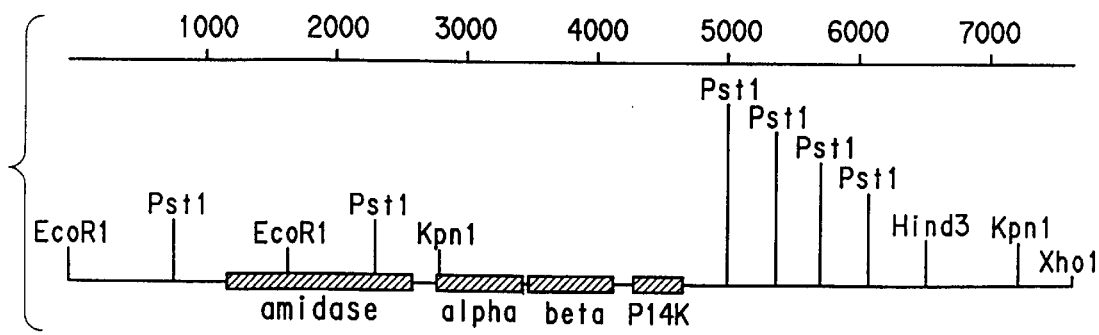

FIG. 10 is a restriction map of an 8 kb nucleic acid fragment showing the 6.5 kb nucleic acid fragment which includes the nitrile hydratase gene isolated from *P. putida* (NRRL-18668), P14K, and the region encoding a *P. putida* (NRRL-18668) amidase enzyme.

Figure 11:
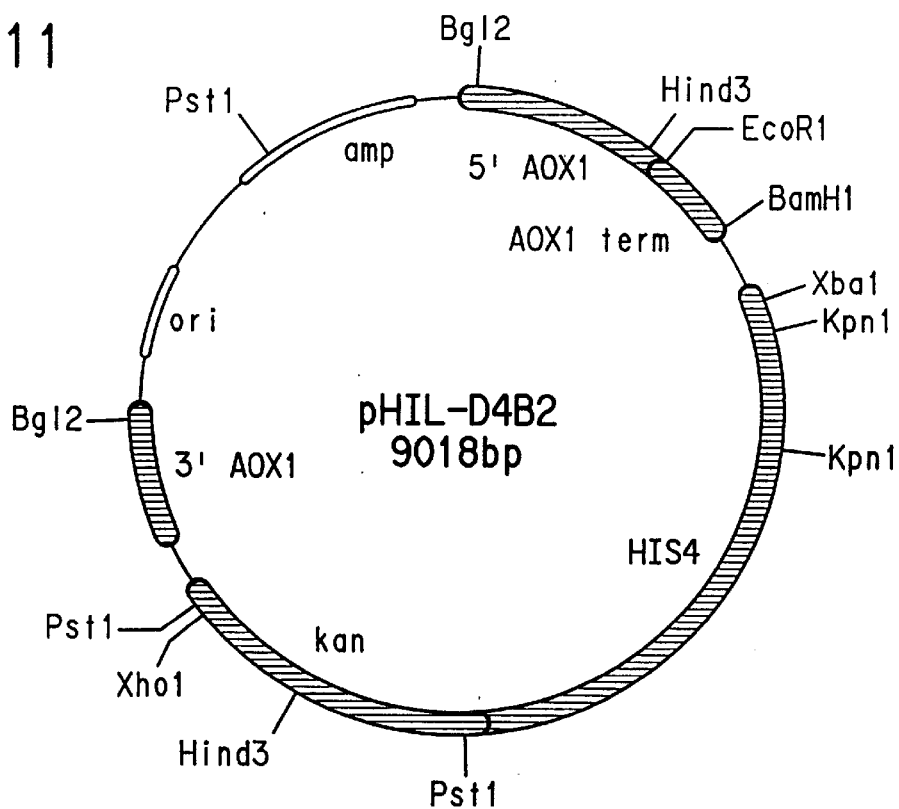

FIG. 11 is a plasmid map of pHIL-D4B2 created by replacing the 0.9 kb EcoR1/Xba1 fragment in pHIL-D4 with the 0.9 kb EcoRl/Xbal fragment from pAO815.

Figure 12:
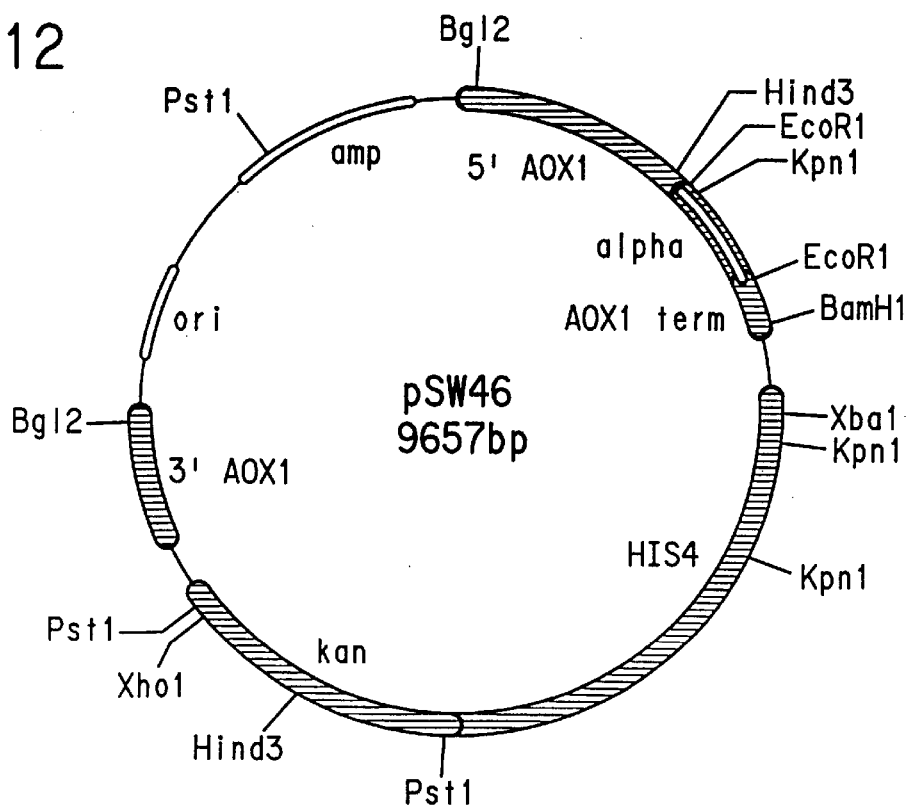

FIG. 12 is a plasmid map of pSW46 created by the insertion of the α gene of the nitrile hydratase enzyme into the EcoR1 site of pHIL-D4B2.

Figure 13:
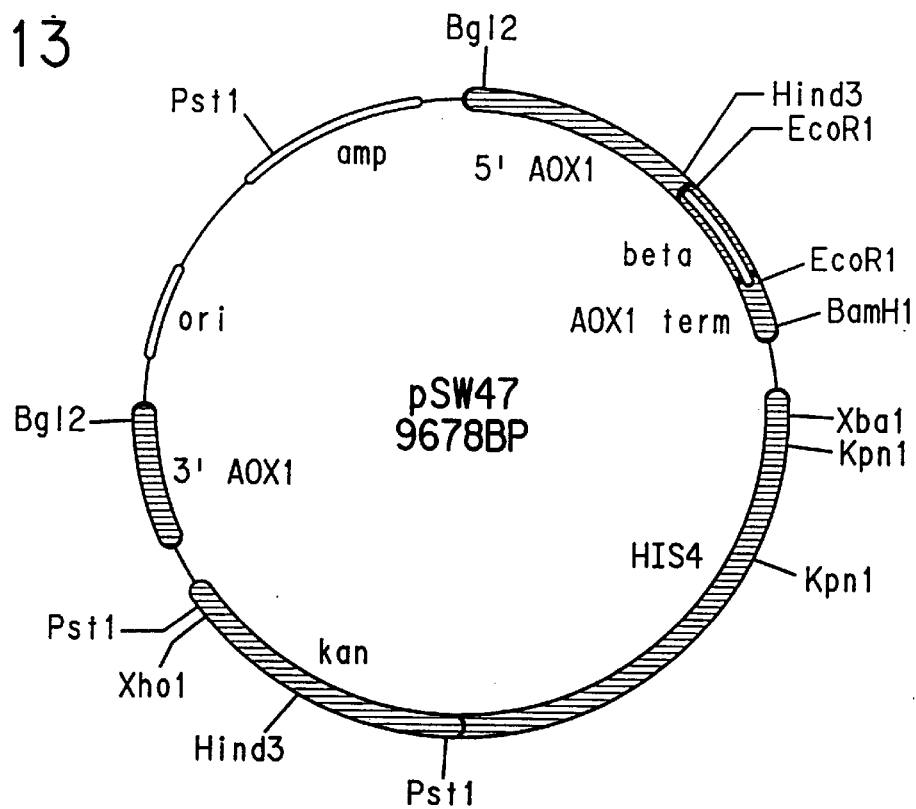

FIG. 13 is a plasmid map of pSW47 created by the insertion of the β gene of the nitrile hydratase enzyme into the EcoR1 site of pHIL-D4B2.

Figure 14:
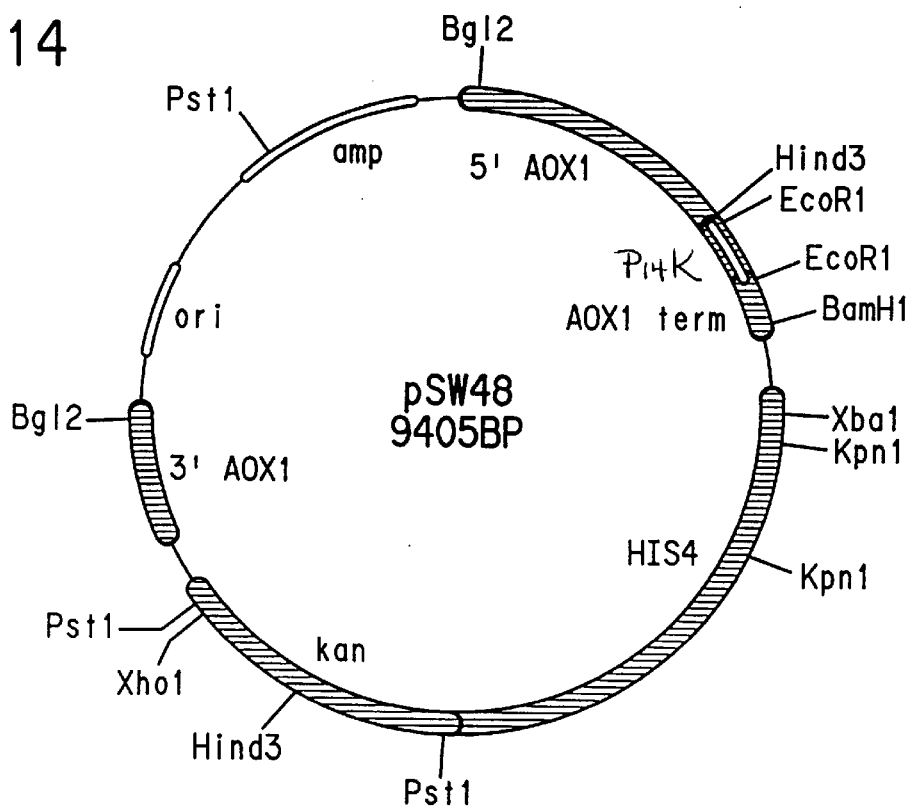

FIG. 14 is a plasmid map of pSW48 created by the insertion of the P14K gene into the EcoR1 site of pHIL-D4B2.

Figure 15:
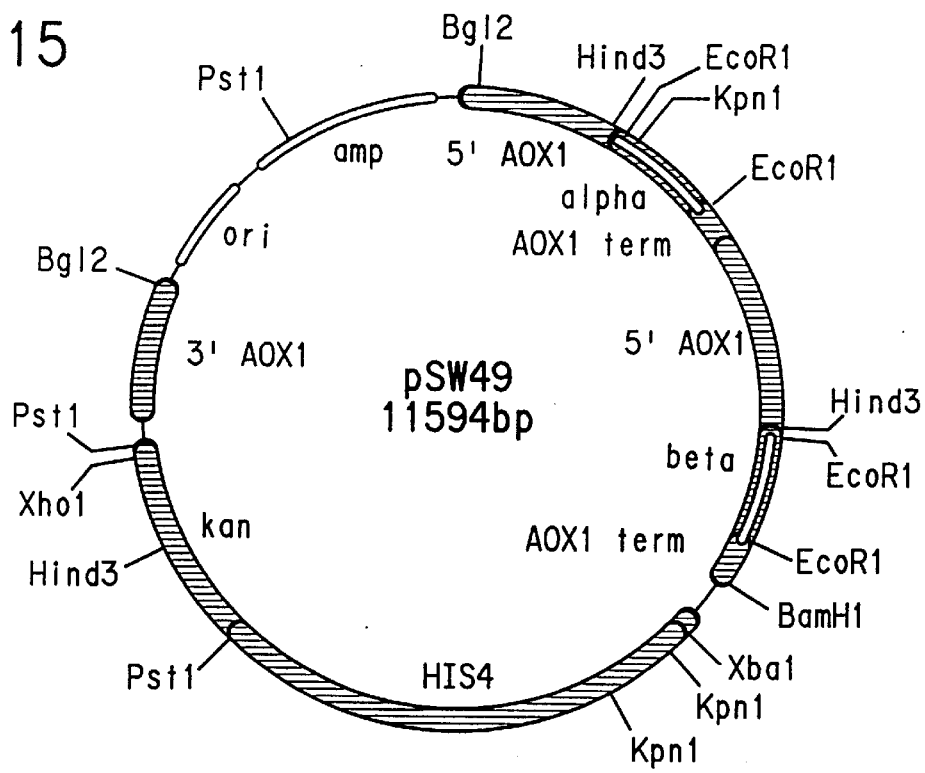

FIG. 15 is a plasmid map of pSW49 containing the α and β expression cassettes from pSW46 and pSW47.

Figure 16:
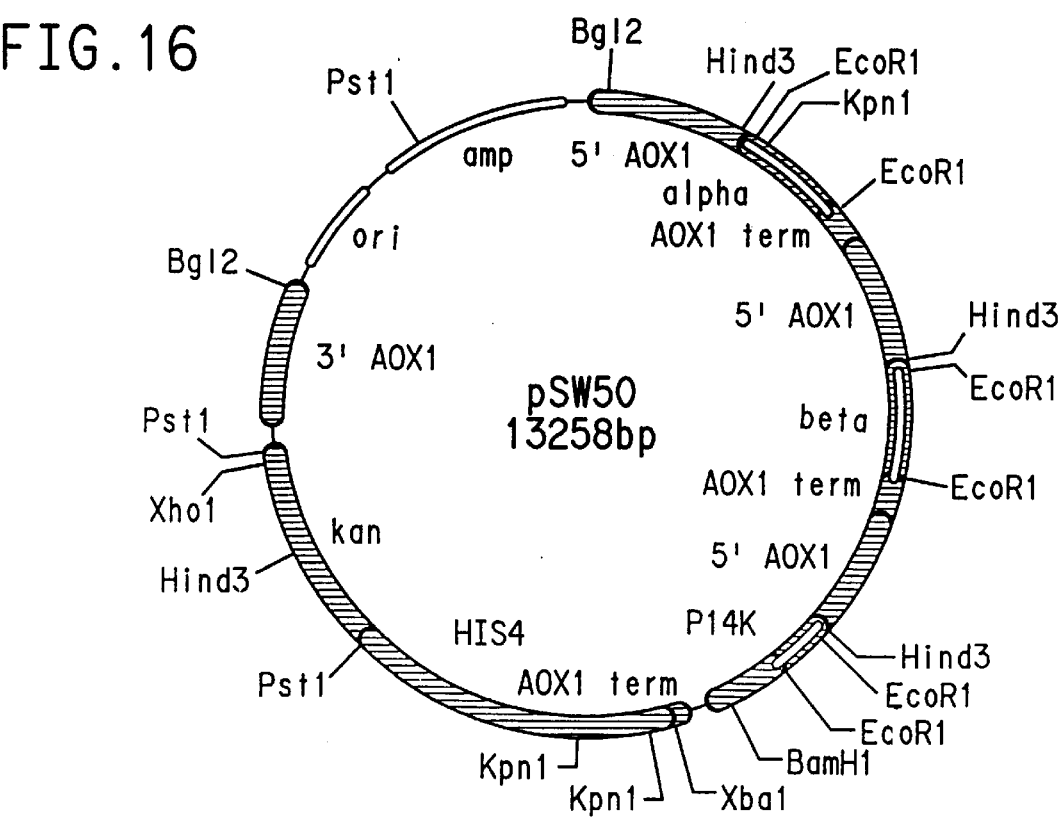

FIG. 16 is a plasmid map of pSW50 containing the α, β and P14K expression cassettes from pSW46, pSW47 and pSW48.

Figure 17:
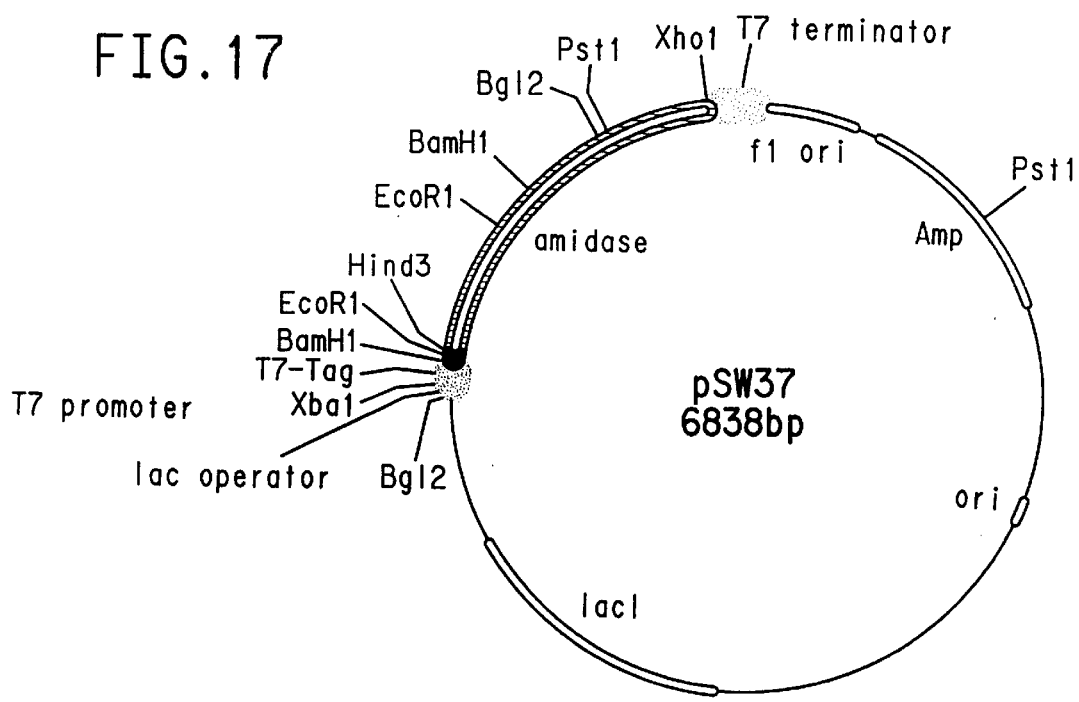

FIG. 17 is a plasmid map of pSW37 containing the expression cassette for the amidase isolated from *P. putida* (NRRL-18668).

Figure 18:
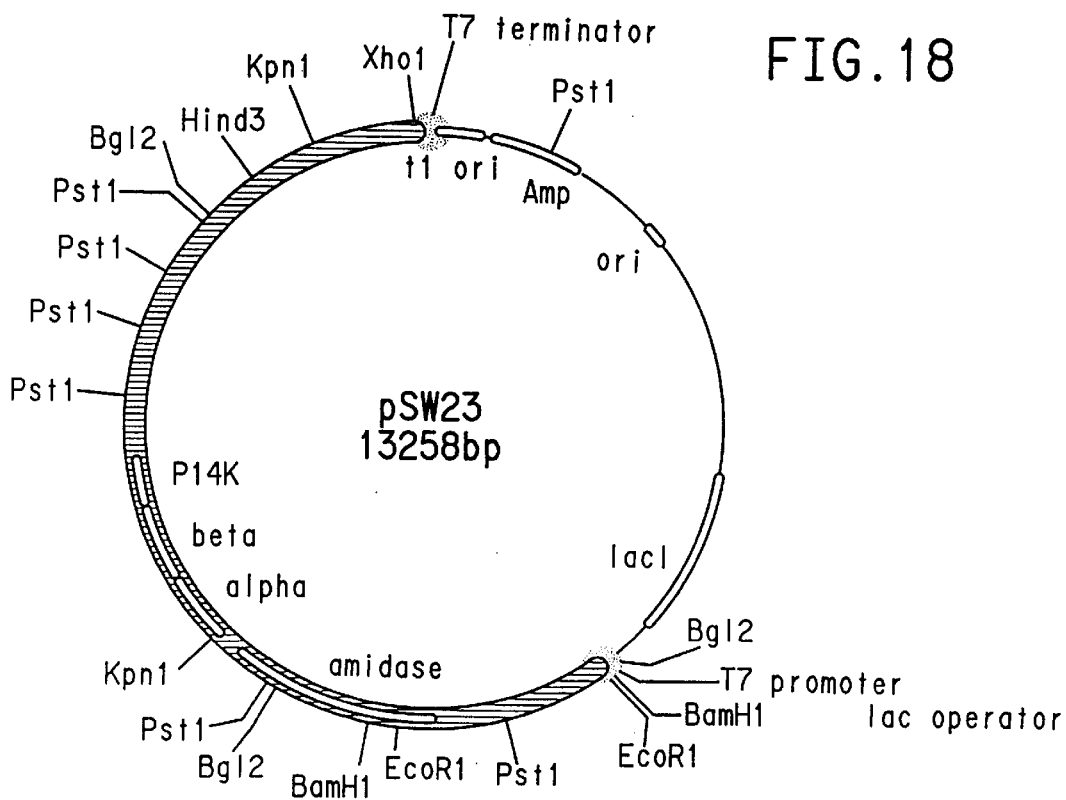

FIG. 18 is a plasmid map of pSW23 containing the expression cassette for the amidase, α, β and P14K isolated from *P. putida* (NRRL-18668).

Applicants have provided sequence listings 1–28 in conformity with 37 C.F.R. 1.821–1.825 and Appendices A and B ("Requirements for Application Disclosures Containing Nucleotides and/or Amino Acid Sequences") and in conformity with "Rules for the Standard Representation of Nucleotide and Amino Acid Sequences in Patent Applications" and Annexes I and II to the Decision of the President of the EPO, published in Supplement No. 2 to OJ EPO, 12/1992.

Applicants have made the following biological deposits under the terms of the Budapest Treaty on the International Recognition of the Deposit of Micro-organisms for the Purposes of Patent Procedure:

| Depositor Identification Reference | Int'l. Depository Designation | Date of Deposit |
| --- | --- | --- |
| *Pseudomonas Putida* | NRRL 18668 | 6 July 1990 |
| *Escherichia coli* SW2 carrying pSW2 | ATCC 69888 | 15 August 1995 |
| *Escherichia coli* SW17 carrying pSW17 | ATCC 69887 | 15 August 1995 |
| *Pichia pastoris* SW50.2 carrying pSW50 | ATCC 74391 | 20 September 1996 |
| *E. coli* SW37 carrying pSW37 | ATCC 98174 | 20 September 1996 |
| *E. coli* SW23 carrying pSW23 | ATCC 98175 | 20 September 1996 |

As used herein, "NRRL" refers to the Northern Regional Research Laboratory, Agricultural Research Service Culture Collection International Depository Authority located at 11815 N. University Street, Peoria, Ill. 61604 U.S.A. The "NRRL No." is the accession number to cultures on deposit at the NRRL.

As used herein, "ATCC" refers to the American Type Culture Collection International Depository Authority located at 10801 University Blvd., Manassas, Va. 20110-2209, U.S.A. The "ATCC No." is the accession number to cultures on deposit with the ATCC.

DETAILED DESCRIPTION OF THE INVENTION

The present invention provides genes derived from *Pseudomonas putida* (NRRL-18668) which encode two polypeptides, which, in combination, have the ability to act as a catalyst to selectively hydrate one nitrile enantiomer in a racemic mixture to produce the chiral amide. This invention also provides a recombinant nucleic acid fragment containing the genes and a set of transformed microbial cell hosts containing the recombinant nucleic acid fragment. The invention further provides a method for the production of the polypeptide catalysts using the transformed microbes and the use of the catalyst in chiral amide production. Additionally, the invention provides for the co-expression in a transformed host of the nitrile hydratase genes with the genes encoding a stereospecific amidase derived from *Pseudomonas chlororaphis* B-23 (FERM B-187) for the production of chiral acids.

The following definitions are used herein and should be referred to for interpretation of the claims and the specification.

Abbreviations:
CPIA—2-(4-chlorophenyl)-3-methylbutyric acid
CPIAm—2-(4-chlorophenyl)-3-methylbutyramide
CPIN—2-(4-chlorophenyl)-3-methylbutyronitrile
GC—Gas Chromatography
HPLC—High-Performance Liquid Chromatography
IPTG—isopropyl-b-D-thiogalatopyranoside
SDS Page—Sodium dodecyl sulfate polyacrylimide gel electrophoresis The term "nitrile hydratase" refers to an enzyme isolated from the bacteria *Pseudomonas putida* (NRRL-18668) which is characterized by its ability to convert a racemic alkyl nitrile to the corresponding enantiomeric R- or S-amide through an intermediate amide where the starting nitrile is:

$$A-\underset{\underset{R^2}{|}}{\overset{\overset{R^1}{|}}{C}}-CN$$

I (R,S)

and wherein:

A is selected from the group consisting of:

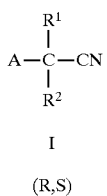
A-1

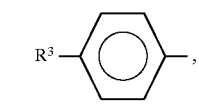
A-2

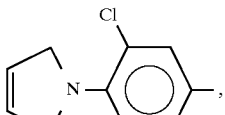
A-3

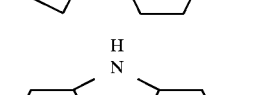
A-4

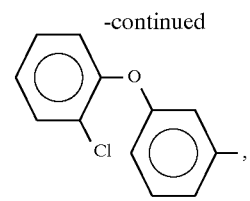
A-5

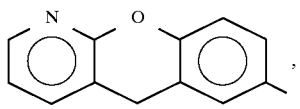
A-6

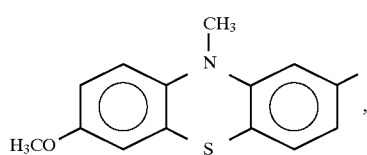
A-7

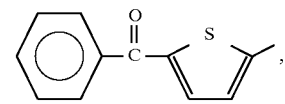
A-8

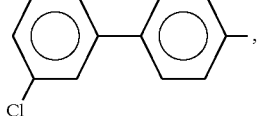

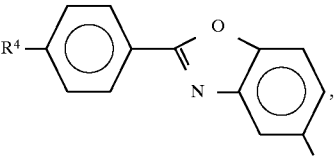

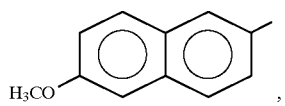
A-9

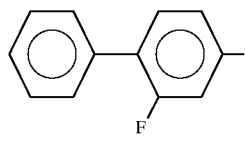
A-10 and

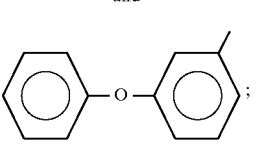
A-11

$R^1$ is $C_1$–$C_4$ alkyl;
$R^2$ is H or OH;
$R^3$ is H, Cl, OCF$_2$H, (CH$_3$)$_2$CHCH$_2$, H$_2$C=C(CH$_3$)CH$_2$NH, $R^4$ is Cl or F.

More specifically, the enzyme has an ability to connect the racemic alkyl nitrile to the corresponding enantiomeric R- or S-alkanoic acid through an intermediate amide.

The instant nitrile hydratase is further defined by the amino acid sequences of its α and β subunits as respectively given in SEQ ID NO.:1 and SEQ ID NO.:2 which are encoded by the α and β nitrile hydratase subunit genes whose base sequences are respectively given by SEQ ID NO.:3 and SEQ ID NO.:4.

The term "amidase" refers to an enzyme naturally found in the bacterium *Pseudomonas putida* B23(FERM B-187) which is characterized by its ability to convert amides of the structure:

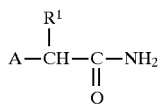

wherein:

A is selected from the group consisting of:

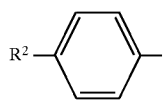

and

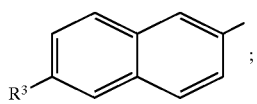

$R^1$ is $C_1$–$C_4$ alkyl;
$R^2$ is H; F; Cl; Br; OH; $C_1$–$C_3$ alkyl; $OCF_2H$; or $H_2C=C(CH_3)CH_2NH$; and
$R^3$ is H; F; Cl; Br; OH; $C_1$–$C_3$ alkyl; or $C_1$–$C_3$ alkoxy;
to the corresponding enantiomeric (R) or (S)-carboxylic acid. The amidase of the instant invention is further identified by the amino acid sequence given in Nishiyama et al., *Bacterial.*, 173:2465–2472 (1991) and the DNA base sequence disclosed in SEQ ID NO.:20.

The term "118668 amidase" refers to an enzyme naturally found in the bacterium *Pseudomonas putida* NRRL-18668 which is characterized by its ability to convert C3 to C6 amides to the corresponding acids. In addition, as described in PCT/DK91/00189, the 18668 amidase is characterized by the ability to convert some (R,S)-aryl-2-alkane nitriles to the corresponding enantiomerically enriched (R) or (S)-carboxylic acid. The amidase of the instant invention is further identified by the amino acid sequence given in SEQ ID NO.:28 and the DNA base sequence disclosed in SEQ ID NO.:27. The "18668 amidasel" is distinct from the amidase isolated from bacterium *Pseudomonas putida* B23(FERM B-187).

The term "P14K gene" refers to a region of the *Pseudomonas putida* NRRL-18668 genome encoding a polypeptide as given by SEQ ID NO.:22 having the base sequence as given by SEQ ID NO.:21, where the expression of the P14K gene is essential for the bioactivity of the *Pseudomonas putida* NRRL-18668 nitrile hydratase enzyme. The term "P14K polypeptide" (or "P14K protein") refers to the active polypeptide encoded by the P14K region.

"Transformation" refers to the acquisition of new genes in a cell by the incorporation of nucleic acid.

The term "nucleic acid" refers to complex compounds of high molecular weight occurring in living cells, the fundamental units of which are nucleotides linked together with phosphate bridges. Nucleic acids are subdivided into two types: ribonucleic acid (RNA) and deoxyribonucleic acid (DNA).

The terms "host cell" and "host organism" refer to a microorganism capable of incorporating foreign or heterologous genes and expressing those genes to produce an active gene product.

The terms "foreign gene", "foreign DNA", "heterologous gene", and "heterologous DNA" refer to genetic material native to one organism that has been placed within a host organism.

The terms "recombinant organism", "transformed host", and "transformed microbial host" refer to an organism having been transformed with heterologous or foreign genes. The recombinant organisms of the present invention express foreign genes encoding active nitrile hydratase and amidase enzymes.

The term "nucleic acid fragment" refers to a fragment of DNA that may encode a gene and/or regulatory sequences preceding (5"non-coding) and following (3"non-coding) the coding region (gene).

The term "expression" refers to the transcription and translation to gene product from a gene coding for the sequence of the gene product, usually a protein.

The terms "plasmid" and "vector" refer to an extra chromosomal element often carrying genes which are not part of the central metabolism of the cell, and usually in the form of circular double-stranded DNA molecules. Such elements may be autonomously replicating sequences, genome integrating sequences, phage sequences, linear or circular, of a single- or double-stranded DNA or RNA, derived from any source.

The term "cassette" refers to a number of nucleotide sequences which have been joined or recombined into a unique construction. An "expression cassette" is specifically comprised of a promoter fragment, a DNA sequence for a selected gene product, and a transcriptional termination sequence.

The terms "restriction endonuclease" and "restriction enzyme" refer to an enzyme which catalyzes hydrolytic cleavage within a specific nucleotide sequence in double-stranded DNA.

The term "promoter" refers to a sequence of DNA, usually upstream of (5' to) the protein coding sequence of a structural gene, which controls the expression of the coding region by providing the recognition for RNA polymerase and/or other factors required for transcription to start at the correct site.

A "fragment" constitutes a fraction of the complete nucleic acid sequence of a particular region. A fragment may constitute an entire gene.

The terms "peptide", "polypeptide" and "protein" are used interchangeably to refer to the gene product expressed.

The terms "encoding" and "coding" refer to the process by which a gene, through the mechanisms of transcription and translation, produces an amino acid sequence. The process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may, in fact, be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (0.1× SSC, 0.1% SDS, 65° C.), with the sequences exemplified herein.

"Homology" refers to the degree to which two nucleic acid fragments contain the same base sequence. "Homology" is determined by the operation of an algorithim and is expressed as a percentage of the base sequence that is the same in both fragments.

Applicants have accomplished the following which are discussed in more detail below and in the Examples:

I. identified and cloned genes for (i) a stereospecific NHase from NRRL-18668, comprising both the α-subunit of the amino acid sequence identified in the Sequence Listing by SEQ ID NO.:1 and the β-subunit of the amino acid sequence identified in the Sequence Listing by SEQ ID NO.:2; (ii) an amidase from NRRL-18668 with deduced amino acid sequence identified in the Sequence Listing by SEQ ID NO.:28; (iii) a gene from NRRL-18668 designated P14K which is essential for NRRL-18668 NHase activity and with deduced amino acid sequence identified in the Sequence Listing by SEQ ID NO.:22;

II. obtained DNA sequences encoding the α-subunit identified in the Sequence Listing by SEQ ID NO.:3; and the β-subunit identified in the Sequence Listing by SEQ ID NO.:4; and the amidase enzyme identified in the Sequence Listing by SEQ ID NO.:27; and the P14K polypeptide identified in the Sequence Listing by SEQ ID NO.:21;

III. constructed recombinant DNA plasmids containing the genes as described in I above located within an 8.0 kb DNA fragment as described in FIG. 10.

Figure 3:
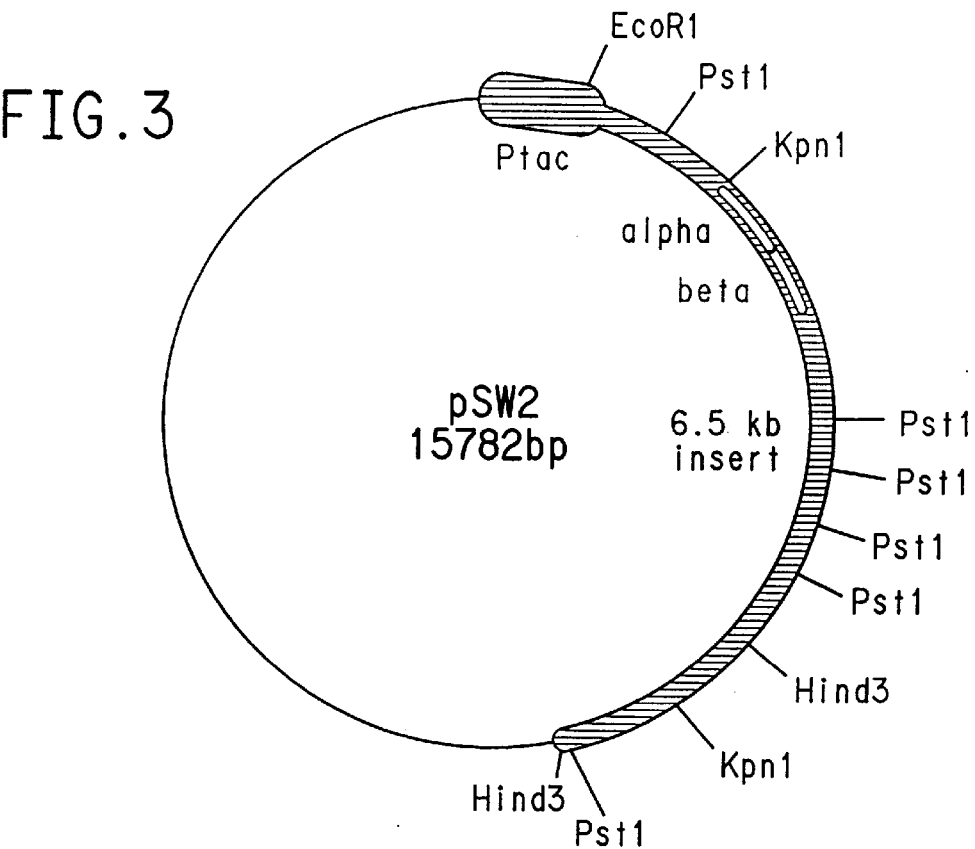
FIG. 3 is a plasmid map of the plasmid pSW2 created by inserting the 6.5 kb DNA fragment comprising the genes encoding the α and β subunits of nitrile hydratase into the wide-host-range vector pMMB207.

IV. transformed microbial hosts with the plasmids described in III above as described in FIGS. 3, 15, and 16;

V. developed a method for the production of stereospecific NHase which comprises growing a transformed host described in IV and recovering the nitrile hydrating activity from the culture;

VI. developed a method for the production of chiral amides which comprises stereospecifically hydrating the nitrile using the nitrile hydrating activity recovered in V;

VII. developed a method for the production of chiral amides which comprises stereospecifically hydrating the nitrile using the nitrile hydrating activity recovered in V for the production of chiral amides using isolated microbial cells as described in IV, the treated matter thereof, or a fixed form of them;

VIII. constructed recombinant DNA plasmids containing the NHase genes as described in I above, in combination with the amidase gene derived from *Pseudomonas chlororaphis* B23 (FERM B-187) or the amidase gene described in I above;

IX. transformed microbial hosts with the plasmids described in VIII above as described in FIGS. 6 and 18;

X. developed a method for the production of NHase and amidase which comprises growing a transformed host described in IX and recovering the nitrile hydrating and amide hydrating activity from the culture; and XI. developed a method for the production of chiral amides and chiral acids which comprises stereoselective hydration of the nitrile and its amide products using the NHase and amidase activities recovered in V for the production of the chiral products using isolated microbial cells as described in IX, the treated matter thereof, or a fixed form of them to produce chiral products.

I. ISOLATION AND CLONING OF THE NITRILE HYDRATASE GENE

A. Isolation and Partial Amino Acid Sequencing of the Nitrile Hydratase Enzyme:

The instant invention provides a nitrile hydratase enzyme which is defined above. The nitrile hydratase of the present invention was isolated and purified from *Pseudomonas putida* (NRRL-18668). Bacterial nitrile hydratases are known to be generally comprised of structurally distinct α and β subunits (Hashimoto et al., *Biosci., Biotechnol., Biochem.*, 58(10), 1859–65 (1994)). The instant nitrile hydratase was separated into α and β subunits using HPLC methodology. Methods for the purification and separation of enzymes by HPLC are common and known in the art. See, for example, Rudolph et al., *Chromatogr. Sci.*, 51 (HPLC Biol. Macromol.), 333–50 (1990).

N-terminal amino acid sequences of each subunit were determined using methods well known in the art. See, for example, Matsudaira, P., *Methods Enzymol.*, 182 (Guide Protein Purif.), 602–13 (1990). Fragments of each subunit were generated and partial amino acid sequences of the fragments were determined. Partial sequences of the α and β subunits of this nitrile hydratase are shown in SEQ ID NOs.:5–9 and 10–13, respectively.

B. DNA Probe fQr Isolation of the Nitrile Hydratase Gene:

In order to isolate the nitrile hydratase gene, a series of degenerate 21-mer oligonucleotide primers based on the available NRRL-18668 NHase amino acid sequence were designed and synthesized for use as polymerase chain reaction (PCR) primers. Genomic DNA was isolated from *P. putida* (NRRL-18668) by standard methods (Sambrook, J., et al., *Molecular Cloning: A Laboratory Manual*, Second Edition, Cold Spring Harbor Laboratory Press (1989)) and was used as a target for PCR with numerous degenerate primer combinations. The resulting amplified products were subjected to Southern analysis (Southern, E. M., *J. Mol. Biol.*, 98, 503, (1975)) using isolated *Rhodococcus rhodochrous* J1 L-NHase gene (Kobayashi, M., *Biochem. Biophys. Acta* 1129:23–33 (1991)) as a probe. One strongly hybridizing fragment of 0.7 kb was identified from a PCR reaction based on the degenerate primers designated D1 and D7. The sequences of D1 and D7 are identified in the Sequence Listing as SEQ ID NO.:14 and SEQ ID NO.:15, respectively. The 0.7 kb PCR fragment was subcloned into the plasmid M13 using standard methods (Sambrook, supra) and sequenced. Sequencing revealed that the 0.7 kb fragment demonstrated a 60% base homology to the *Rhodococcus rhodochrous* J1 L-NHase gene. Deduced amino acid sequence from this 0.7 kb fragment was compared to available NRRL-18668 amino acid sequences determined previously and to other known NHase sequences. The comparison confirmed that this fragment was part of the *P. putida* NHase gene. The 0.7 kb DNA fragment was sequenced and is identified as SEQ ID No.:16. The 0.7 kb fragment was used as a probe to isolate a genomic DNA fragment from NRRL-18668 which contains the entire NHase gene.

C. Isolation of a Genomic DNA Fragment Containing NRRL-18668 NHase Gene:

Genomic DNA isolated from *P. putida* (NRRL-18668) was digested with restriction enzymes EcoR1 and Xho1 and size-selected by agarose gel electrophoresis based on Southern blotting using the 0.7 kb DNA fragment described above as a probe. Restricted genomic DNA was then cloned into phage lambda ZAPII [Stratagene, La Jolla, Calif.]. The lambda library was screened with the 0.7 kb DNA fragment probe and one positively hybridizing phage clone with a DNA insert of 6.5 kb was identified and isolated.

Figure 1:
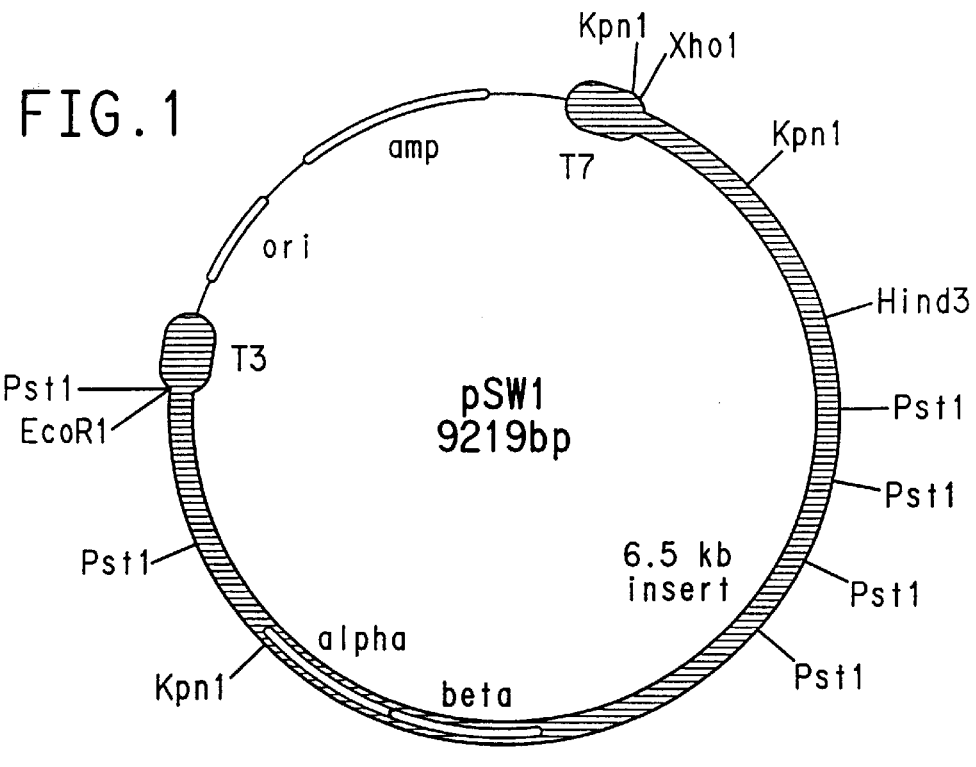
FIG. 1 is a plasmid map of the plasmid pSW1 containing a 6.5 kb DNA fragment which encodes the α and β subunits of the nitrile hydratase enzyme isolated from *P. putida* (NRRL-18668).

D. Plasmid Construction and Host Transformation and Confirmation of NHase Sequence:

Once a positive clone containing a 6.5 kb insert was identified, the presence of the NHase gene in the clone was confirmed by a process of (i) constructing a plasmid containing the 6.5 kb insert (pSW1, FIG. 1); (ii) transforming a suitable host cell with this plasmid; (iii) growing up the transformed host and purifying the plasmid DNA; (iv) constructing a restriction map from the purified DNA (FIG. 2); and (v) sequencing the NHase genes. The confirmation process is common and well known in the art and techniques used may be found in Sambrook supra.

Sequence analysis confirmed the nitrile hydratase coding regions, which consisted of two open reading frames corresponding to the alpha and beta subunits of the corresponding NHase protein as defined in the Sequence Listing by SEQ ID NO.:17 and FIG. 7. The α and β open reading frames were analyzed for base sequence similarly to the *Rhodococcus rhodochrous* J1 L-NHASE gene used as a probe and described above. Homology comparisons showed that the α open reading frame had 64% homology to the region encoding the α subunit on the J1 gene and the β open reading frame had 52% homology to the region encoding the β subunit on the J1 gene.

II. CONSTRUCTION OF EXPRESSION VECTOR AND EXPRESSION STRAINS

The present invention provides a transformed host cell capable of expressing active nitrile hydratase enzyme. Generally, it is preferred if the host cell is an *E. coli*, however, it is not outside the scope of the invention to provide alternative hosts. Such alternative hosts may include, but are not limited to, members of the genera Pseudomonas, Rhodococcus, Acinetobacter, Bacillus, Saccharomyces, Pichia, Aspergillus, Hansenula, and Streptomyces.

The present invention provides a variety of plasmids or vectors suitable for the cloning of the nitrile hydratase gene in the desired host. Suitable vectors for construction contain a selectable marker and sequences allowing autonomous replication or chromosomal integration. Additionally, suitable vectors for expression contain sequences directing transcription and translation of the heterologous DNA fragment. These vectors comprise a region 5' of the heterologous DNA fragment which harbors transcriptional initiation controls, and optionally a region 3' of the DNA fragment which controls transcriptional termination. It is most preferred when both control regions are derived from genes homologous to the host cell, although such control regions need not be derived from the genes native to the specific species chosen as a production host. Suitable vectors can be derived, for example, from a bacteria (e.g., pET, pBR322, pUCl9, pSP64, pUR278 and pORFl), a virus (such as bacteriophage T7 or a M-13 derived phage), a cosmid, a yeast or a plant. Protocols for obtaining and using such vectors are known to those in the art. (Sambrook, supra.)

Vectors suitable for *E. coli* will have compatible regulatory sequences and origins of replication. They will be preferably multicopy and have a selectable marker gene, for example, a gene coding for antibiotic resistance.

Promoters useful for driving the expression of heterologous DNA fragments in *E. coli* are numerous and familiar to those skilled in the art. Virtually any promoter capable of driving the gene encoding the nitrile hydratase enzyme is suitable for the present invention, although promoters native to *E. coli* are preferred and the inducible IPTG Ptac promoter is most preferred (deBoer, H., *Proc. Natl. Acad. Sci. USA*, 80:21–25 (1983). Although an inducible promoter is preferred, one of skill in the art will appreciate that either inducible or constitutive promoters are suitable.

Figure 4:
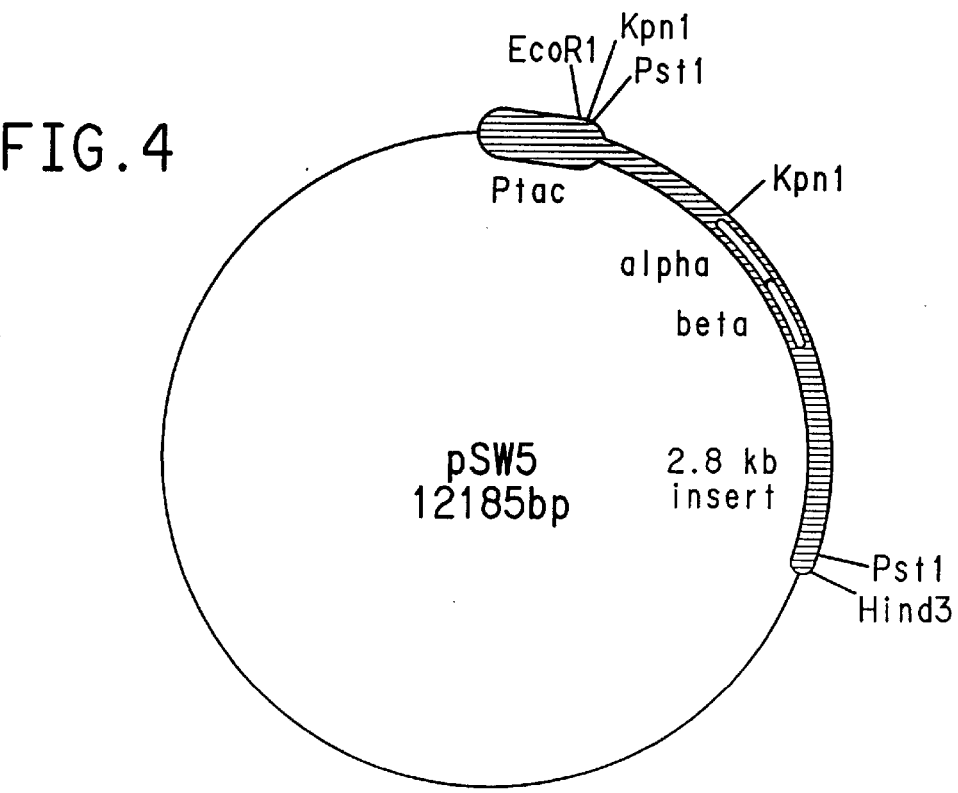
FIG. 4 is a plasmid map of the plasmid pSW5 created by inserting a 2.8 kb subclone of the 6.5 kb nucleic acid fragment comprising the genes encoding the α and β subunits of nitrile hydratase into the wide-host-range vector pMMB207.

Within the context of the present invention the entire 6.5 kb DNA insert containing the NRRL-18668 NHase gene in the plasmid pSW1 was subcloned into the wide-host-range vector pMMB207 (Bagdasarian, M., *Gene*, 97:39–47 (1991)) under the control of the Ptac promoter to create an expression vector designated pSW2 (FIG. 3). Additionally, the 2.8 kb Pst1 DNA fragment derived from the 6.5 kb DNA fragment and containing the NRRL-18668 NHase gene but with substantially less upstream and downstream flanking sequence, was also subcloned into the vector pMMB207 under the control of the Ptac promoter to generate the plasmid pSW5 (FIG. 4). Comparing these two expression constructs allowed Applicants to investigate proximal accessory sequences or proteins which might be involved in expression or activity of NHase. Applicants' studies indicated that the NHase genes may be part of an operon which generates a 10 kb mRNA transcript, of which only approximately 1.5 kb is accounted for by NHase. This suggests that additional genes are encoded by the upstream and downstream sequence flanking NHase. Others have described a requirement for downstream sequence for efficient expression of NHase in *Rhodococcus* sp. N-774 (Hashimoto, Y., *Biosci. Biotech. Biochem.*, 58:1859–1865 (1994)).

Following cloning, *E. coli* XL1-Blue host was transformed in parallel with the plasmid pSW2 or pSW5 described above. Methods of transforming host cells with foreign DNA are common and well known in the art. For example, transforming host cells with foreign DNA may be accomplished using calcium-permeabilized cells, electroporation, or by transfection using a recombinant phage virus. (Sambrook supra). Plasmid DNA was isolated from these transformants and enzyme restriction analysis confirmed the construction of two separate strains, one harboring the pSW2 plasmid and the other harboring the pSW5 plasmid.

The gene encoding the α subunit, and the gene encoding the β subunit of NRRL-18668 NHase were also expressed in an alternative host, the methylotrophic yeast *Pichia pastoris*. Methods for producing heterologous proteins in *P. pastoris* are well known in the art. For each subunit, the coding sequence was placed under control of the methanol inducible promoter, alcohol oxidase I (AOX1), in a vector which was subsequently integrated into the host chromosome. Each subunit was produced in the respective host after induction by methanol. NHase activity was not reproducibly obtained upon mixing extract prepared from the α producing strain with extract prepared from the β producing strain. In addition, a single strain producing both α and β subunits under control of the AOX1 promoter was constructed. Both subunits were produced in this recombinant *P. pastoris* strain, but NHase activity was not obtained.

Applicants sequenced DNA both upstream and downstream of the NHase genes, and identified at least two open reading frames, one upstream and one downstream. The upstream open reading frame was determined to encode an amidase enzyme, based on comparison of the deduced amino acid sequence to other amidase amino acid sequences. Plasmids were constructed for the expression of NRRL-18668 amidase in E. coli. A search of the protein database with the deduced amino acid sequence encoded by the downstream open reading frame (designated P14K) indicated no significant matches. Plasmids were constructed for expression of NHase genes only or NHase and P14K genes in both E. coli and P. pastoris. In both E. coli and P. pastoris, NHase activity was obtained only when P14K was co-expressed with the NHase genes. The preference for hydrolysis of S-nitriles (stereo-specificity) observed in the native organism was also demonstrated in the recombinant orgamisms producing active NHase.

III. EXPRESSION OF THE NITRILE HYDRATASE ENZYME AND CONVERSION OF SUBSTRATES

Transformed E. coli cells harboring plasmid pSW2 under the control of the IPTG inducible Ptac promoter, were grown under standard conditions and induced to express the nitrile hydratase enzyme. Cells were harvested and lysed and the protein was detected in crude lysates by SDS-polyacrylamide gel electrophoresis followed by western blot analysis (Egger et al., Mol. Biotechnol., 1(3), 289–305 (1994)) using antisera raised against NRRL-18668 NHase protein (FIG. 5). Under these conditions induced cells produced approximately 10-fold as much nitrile hydratase protein as uninduced cells. Nitrile hydratase was not detected from a control strain harboring the vector pMMB207 without the 6.5 kb insert.

Nitrile hydratase is typically confirmed by incubating a suitable substrate nitrile in the presence of the crude or purified enzyme. Suitable substrates for the instant hydratase include a variety of racemic alkyl nitriles such as methacrylonitrile, methylbutyronitrile and propionitrile. In the instant case, nitrile hydratase activity was confirmed by monitoring the conversion of methacrylonitrile to the corresponding amide. Induced cells harboring the plasmid pSW2 showed rapid conversion of methacrylo-nitrile, while induced cells without the pSW2 plasmid showed no conversion of methacrylonitrile. Additionally, induced cells harboring the plasmid pSW5 show no conversion of methacrylonitrile.

Stereospecific activity of the enzyme produced in induced cells harboring plasmid pSW2 was confirmed by monitoring the conversion of R,S-CPIN to amide products using reverse-phase or chiral high pressure liquid chromatography (HPLC). Methods of enantiomer separation on HPLC are well known in the art. See, for example, Mutton, I., Pract. Approach Chiral Sep., Liq. Chromatogr., 329–55 (1994), Editor(s): Subramanian, Ganapathy, Publisher: VCH, Weinheim, Germany.

IV. CO-EXPRESSION OF NITRILE HYDRATASE AND AMIDASE

The present invention further provides a transformed microorganism capable of co-expressing both a heterologous nitrile hydratase gene and a heterologous amidase gene. This transformant is capable of effecting the conversion of racemic mixtures of aryl-2-alkane nitriles to the corresponding carboxylic acids via the amide intermediate.

A number of amidase encoding genes may be suitable for co-expression with the instant nitrile hydratase. However, the amidase gene isolated from Pseudomonas chlororaphis B23 and defined above is preferred.

The gene encoding the Pseudomonas chlororaphis B23 amidase is known (Nishiyama, M. J., Bacteriol., 173:2465–2472 (1991)) and was obtained through PCR amplification using appropriate primers. The amplified gene comprising 1.5 kb was subcloned into a pMMB207 plasmid (already containing the nitrile hydratase gene) using standard restriction enzyme digestion and ligation techniques (Sambrook supra) to generate the plasmid pSW17 (FIG. 6). The plasmid pSW17 was constructed so as to place the amidase gene and the nitrile hydratase gene both under the control of the same IPTG inducible Ptac promoter. The plasmid pSW17 was then used to transform a suitable host cell (e.g., E. coli XL1-Blue) according to standard methods.

In order to confirm the activity of the amidase produced in cells transformed with plasmid pSW17, cells transformed by plasmid pSW17 were grown up and induced with IPTG in the presence of a suitable nitrile and the chiral amide and free acid products were identified by chiral HPLC analysis.

The following Examples are meant to illustrate the invention but should not be construed as limiting it in any way.

EXAMPLE 1

Isolation, Purification, and Amino Acid Sequencing of Portions of the Nitrile Hydratase α and β Subunits Pseudomonas putida (NRRL-18668) was cultured in a medium (10 g/L glucose, 8.7 g/L $K_2HPO_4$, 6.8 g/L $KH_2PO_4$, 2.0 g/L acetonitrile, 1.85 g/L $NaNO_3$, 0.50 g/L $MgSO_4.7H_2O$, 0.050 g/L $FeSO_4.7H_2O$, 0.30 mg/L $MnCl_2.4H_2O$, 0.10 mg/L $H_3BO_3$, 0.050 mg/L $NiSO_4.6H_2O$, 0.050 mg/L $CuSO_4.5H_2O$, 0.050 mg/L $Co(NO_3)_2.6H_2O$, 0.030 mg/L $Na_2MoO_4.2H_2O$, 0.030 mg/L $ZnSO_4.4H_2O$, 0.020 mg/L KI, 0.020 mg/L KBr, 0.010 mg/L pyridoxine.HCl, 0.0050 mg/L thiamine.HCl, 0.0050 mg/L D-pantothenate, $Ca^{2+}$ salt, 0.0050 mg/L riboflavin, 0.0050 mg/L nicotinic acid, 0.0050 mg/L p-aminobenzoic acid, 0.0020 mg/L biotin, 0.0020 mg/L vitamin $B_{12}$, 0.0020 mg/L folic acid, pH 7.0) at 30° C. for 48 h. The bacterial cells were harvested. 100 g of the bacterial cells were disrupted and the cell free extract fractionated with ammonium sulfate. The ammonium sulfate fractionation precipitate was dissolved in buffer and loaded on a Phenyl Sepharose CL-4B chromatography column (Pharmacia Biotech, Uppsala, Sweden), followed by a DEAE-cellulose chromatography column, and a second DEAE-cellulose chromatography column (Whatman, Maidstone, England). Active fractions were pooled and concentrated. The concentrate containing the enzyme was loaded on a reverse phase high performance chromatography column (Vydac 208TP104) and two subunits (α and β) were obtained. The N-terminal amino acid sequence of the α- and β-subunits was determined using an amino acid sequencer (Beckman model LF3000G gas phase protein sequencer, Fullerton, Calif. The α- and β-subunits were cleaved separately using cyanogen bromide, TPCK-treated trypsin, and AspN protease, and the peptides generated were separated on a reverse phase high performance chromatography column (Vydac 208TP104, The Separations Group, Hesperia, Calif.). Fractions containing well-resolved peptides were sequenced using the same technique. The sequences of the individual peptides were combined into partial sequences of the subunits by alignment with the published sequences of the α- and β-subunits of nitrile hydratases from *P. chlororaphis* B23 [Nishiyama et al., *J. Bacteriol.*, 173:2465–2472 (1991)], Rhodococcus N-774 [Ikehata et al., *Eur. J. Biochem.*, 181:563–570 (1989)], and *Rhodococcus rhodochrous* J1 [Kobayashi et al., *Biochim. Biophys. Acta*, 1129:23–33 (1991)]. The partial sequences of the of the α- and β-subunits of nitrile hydratase from *Pseudomonas putida* (NRRL-18668) were identified as defined in the Sequences Listing as SEQ ID NOs.:5–9 and SEQ ID NOs.:10–13, respectively.

EXAMPLE 2

Preparation of DNA Probe for NRRL-18668 NHase Gene

The degenerate oligonucleotide designated D1 as defined in the Sequence Listing as SEQ ID NO.:14, and the degenerate oligonucleotide designated D7 as defined in the Sequence Listing as SEQ ID NO.:15 were used as primers in a polymerase chain reaction (PCR) [Mullis, K. B., *Meth. Enzymol.*, 155:335–350 (1987)] with NRRL-18668 genomic DNA as target. PCR conditions were as follows: 100 ng target, 1 μM each primer, 200 μM each of dATP, dCTP, dGTP, dTTP, 10 mM Tris-HCl pH 8.3, 50 mM KCl, 1.5 mM $MgCl_2$, 0.001% gelatin, 25 U/mL Amplitaq™ DNA polymerase (Perkin Elmer Cetus, Norwalk, Conn.). PCR parameters were as follows: 94° C. 1 min, 55° C. 1 min, 72° C. 1 min, 40 cycles. One half of the PCR product was subjected to ethidium bromide agarose gel electrophoresis followed by transfer to nitrocellulose and Southern analysis with $^{32}P$ labeled *Rhodococcus rhodochrous* J1 L-NHase gene as probe [Southern, E. M., *J. Mol. Biol.*, 98:503 (1975)]. Strong hybridization of a DNA fragment of approximately 0.7 kb suggested the presence of at least a portion of a NHase gene in this PCR product. The remaining half of the PCR product was restricted with EcoR1 (the primers were designed with EcoR1 sites at the 5' ends) and ligated to EcoR1 restricted M13 mp19 vector DNA. Ligation mix was used to transfect competent *E. coli* XL1-Blue which was plated onto LB plates supplemented with IPTG and X-gal (5-bromo-4chloro-3indolyl-β-D-galactopyranoside) [Maniatis, T., Molecular Cloning: A Laboratory Manual (1989)]. Phage DNA was prepared from several "white" plaques [Maniatis, T., Molecular Cloning: A Laboratory Manual (1989)] and sequenced by dideoxy termination protocol using universal primer [Sanger, F., *Science*, 214:1205–1210 (1981)]. Analysis of the nucleotide sequence obtained as defined in the Sequence Listing as SEQ ID NO.:16 confirmed that the PCR product corresponds to part of the NHase gene.

EXAMPLE 3

Isolation of Genomic DNA Fragment Containing NRRL-18668 NHase Gene

Total genomic DNA (10 pg) from NRRL-18668 was isolated [Maniatis, T., Molecular Cloning: A Laboratory Manual (1989)], restricted with EcoR1 and Xho1, and one half subjected to agarose gel electrophoresis followed by Southern blot using the $^{32}P$ labeled 0.7 kb fragment described in Example 2 as a probe [Southern, E. M., *J. Mol. Biol.*, 98:503 (1975)]. A strongly hybridizing band of approximately 6.5 kb was identified, suggesting that the NHase gene (or part of it) resides on this 6.5 kb genomic DNA fragment. A duplicate agarose gel was run and a gel slice from the 6.5 kb region was excised. DNA extracted from the gel slice isolated [Maniatis, T., Molecular Cloning: A Laboratory Manual (1989)] was ligated to lambda DNA restricted with EcoR1 and Xho1. The ligation mix was packaged into phage particles and used to transfect *E. coli* XL1-Blue according to the manufacturer's instructions [Stratagene, La Jolla, Calif.]. Several thousand plaques were screened using the $^{32}P$-labeled 0.7 kb fragment as probe [Maniatis, T., Molecular Cloning: A Laboratory Manual (1989)]. One positively hybridizing plaque was subsequently purified.

EXAMPLE 4

Construction of Plasmid Containing NRRL-18668 NHase Gene

DNA from the purified phage plaque described in Example 3 was excised and converted to a pBluescript-based plasmid according the the manufacturer's instructions [Stratagene, La Jolla, Calif.], and designated pSW1. The plasmid pSW1 has a 6.5 kb insert containing the NRRL-18668 NHase gene as described in FIG. 1.

EXAMPLE 5

Transformation of Host by Plasmid Containing NRRL-18668 NHase Gene

The plasmid pSW1 described in Example 4 was used to transform competent *E. coli* XL1-Blue cells by the $CaCl_2$ method [Maniatis, T., Molecular Cloning: A Laboratory Manual (1989)].

EXAMPLE 6

Figure 2:
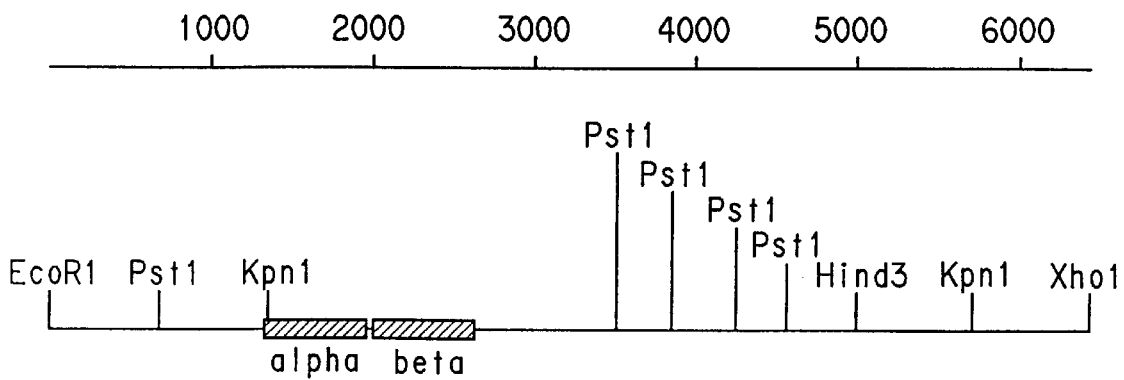
FIG. 2 is a restriction map of the 6.5 kb nucleic acid fragment which includes the nitrile hydratase gene isolated from *P. putida* (NRRL-18668) showing the location of the α and β subunits.

Recombinant Plasmid Purification and Construction of Restriction Map for Genomic DNA Fragment Containing NRRL-18668 NHase Gene Plasmid DNA purified by the alkaline lysis method [Maniatis, T., Molecular Cloning: A Laboratory Manual (1989)] from *E. coli* cells harboring plasmid pSW1, described in Example 5, was restricted with EcoR1, Pst1, Kpn1, Hind3, and Xho1 singly or in various combinations, followed by agarose gel analysis, and Southern analysis using the 0.7 kb PCR product described in Example 2 as a probe [Southern, E. M., *J. Mol. Biol.*, 98:503 (1975)]. A restriction map constructed for the 6.5 kb insert fragment of the plasmid pSW1, including the location of the NHase gene is shown in FIG. 2.

EXAMPLE 7

DNA Sequencing of NRRL-18668 NHase Gene

Based on the restriction map described in Example 6, the nucleotide sequence of a fragment of DNA encompassing the NHase gene was determined by the Sanger dideoxy method [Sanger, F., *Science*, 214:1205–1210 (1981)] using double-stranded plasmid DNA as template. The nucleotide sequence and the corresponding predicted amino acid sequences for the α and β peptides are defined in the Sequence Listing as SEQ ID NO.:17 and FIG. 7.

EXAMPLE 8

Construction of NRRL-18668 NHase Expression Vector

Plasmid pSW1 was restricted with EcoR1 and Xho1 and the 6.5 kb fragment was ligated to the wide host range plasmid pMMB207 [Bagdasarian, M., *Gene*, 97:39–47

(1991)] restricted with EcoR1 and Sal 1 to generate the plasmid designated pSW2 and shown in FIG. 3. The 2.8 kb Pst1 DNA fragment containing the NRRL-18668 NHase gene was excised from plasmid pSW2 by digestion with Pst1 restriction enzyme and ligated into the Pst1 site of vector pMMB207 to generate the plasmid designated pSW5 and shown in FIG. 4.

EXAMPLE 9

Construction of NRRL-18668 NHase Expression Strain

Plasmids pSW2 and pSW5 described in Example 8 were used to transform competent *E. coli* XL1-Blue cells which were plated onto LB plates supplemented with 12.5 µg/mL chloramphenicol [Maniatis, T., Molecular Cloning: A Laboratory Manual (1989)].

EXAMPLE 10

Expression of NRRL-18668 NHase Protein

*E. coli* cells harboring plasmid pSW2, described in Example 8A, were grown in SOC media (0.5 g/L NaCl, 20 g/L bacto-tryptone, 5 g/L bacto-yeast extract, 20 mM glucose, 2.5 mM KCl, 10 mM $MgCl_2$) at 37° C. to OD600= 0.5, followed by induction at 30° C. by the addition of IPTG to 1 mM. After induction times ranging from 0.5 h to 3 h, cells were harvested by centrifugation, and suspended in 1/10 volume PBS (8.0 g/L NaCl, 0.2 g/L KCl, 1.44 g/L $Na_2HPO_4$, 0.24 g/L $KH_2PO_4$ pH 7.4). A cell suspension equivalent to 0.05 OD600 units is added to an equal volume of 2× SDS gel-loading buffer (100 mM Tris pH 6.8, 200 mM DTT, 4% SDS, 0.2% bromophenol blue, 20% glycerol), boiled for 5 min, and analyzed by SDS PAGE [Laemmli, U.K., *Nature*, 227:680–685 (1970)] followed by western blot [Towbin, H., *Proc. Natl. Acad. Sci.*, 76:4350–4354 (1979)] using antisera raised against NRRL-18668 NHase protein. A positive signal was obtained at approximately 28 kd and corresponded to purified NHase protein as shown in FIG. 5.

EXAMPLE 11

Expression of Active NRRL-18668 NHase

*E. coli* cells harboring plasmid pSW2, described in Eample 9, were grown and induced as described in Example 9 in a 500 mL batch. Cells were harvested by centrifugation and washed with pH 7.2, 0.1M phosphate buffer($KH_2PO_4$ adjusted with 50% NaOH) containing 15% glycerol. Washed cells were stored frozen at −70° C. Washed and frozen *E. coli* cells harboring the pSW2 plasmid and were suspended in 100 mM phosphate buffer, pH 7, at a cell density of $O.D._{490}=0.62$. Methacrylo-nitrile was added to a final concentration of 10 mM and the mixture was shaken at 250 rpm at room temperature. Analysis of supernatant showed that methacrylonitrile was rapidly converted to hydrolysis products after 30 min. Cells without the pSW2 plasmid showed no activity.

EXAMPLE 12

Production of Chiral Amides

Induced *E. coli* cells harboring the pSW2 plasmid and producing stereospecific nitrile hydratase activity as described in Example 11 were suspended in 100 mM phosphate buffer, pH 7, and a concentration of 50 mg/mL. One milliliter of this suspension was placed in a glass vial containing 19.3 mg of R,S-CPIN. The suspension was shaken at 250 rpm on a rotary shaker at room temperature for 68 h. Analysis by chiral HPLC reveals only the S-CPIAm was produced from the R,S-CPIN.

|  | mg nitrile | | mg amide | |
|---|---|---|---|---|
| Time, h | R-CPIN | S-CPIN | R-CPIAm | S-CPIAm |
| 0 | 9.6 | 9.6 | 0 | 0 |
| 68 | 9.6 | 5.5 | 0 | 4.5 |

EXAMPLE 13

Construction of a Vector for Co-Expression Of NRRL-18668 NHase and Pseudomonas Chlororaphis B23 Amidase The amidase gene from *Pseudomonas chlororaphis* B23 (defined as SEQ ID NO.:20) was obtained through PCR amplification using primers with overhanging 5' EcoR1 sites as defined in the Sequence Listing as SEQ ID NO.:18 and SEQ ID NO.:19. This 1.4 kb DNA fragment containing the B23 amidase gene was digested with EcoR1 restriction enzyme and ligated into the EcoR1 site of pMMB207, and the 5.0 kb EcoR1/Hind111 DNA fragment from pSW1, described in Example 4, was subcloned between the Xba1 and Hind111 to generate the plasmid pSW17 as shown in FIG. 6.

EXAMPLE 14

Construction of Strain for Co-Expression of NRRL-18668 NHase and Pseudomonas Chlororaphis B23 Amidase Plasmid pSW17 described in Example 13 was used to transform competent *E. coli* XL1-Blue cells which were selectively grown on LB plates supplemented with 12.5 µg/mL chloramphenicol [Maniatis, T., Molecular Cloning: A Laboratory Manual (1989)].

EXAMPLE 15

Comparison of NHase Activity from pSW2 and pSW5

*E. coli* cells harboring the pSW2 or pSW5 plasmid and induced according to the protocol in Example 11 were each suspended separately in 100 mM phosphate buffer, pH 7, at a concentration of 20 mg/mL. Butyronitrile was added to each suspension to a final concentration of 10 mM. The suspensions were shaken at 250 rpm on a rotary shaker at room temperature for 24 h. At the end of the incubation period, 0.1% phosphoric acid was added to the suspensions, bringing them to a pH of 2–3 and stopping nitrile hydratase activity. Cells were removed from the suspension by centrifugation. Analysis of the reactions showed the following products:

pSW2—94% butyramide, 6% butyronitrile;
pSW5—<1% butyramide, 100% butyronitrile.

EXAMPLE 16

Production of S-CPIAm and S-CPIA from R,S-CPIN

*E. coli* cells harboring the pSW17 and induced according to the protocol in Example 11 were suspended in 100 mM phosphate buffer, pH 7, at a concentration of 100 mg/mL. One milliliter of this suspension was placed in a glass vial containing 19.3 mg of R,S-CPIN dispersed in a dry form on 0.5 g of 0.5 mm glass beads. The suspension was shaken in a 20 mL scintillation vial at 250 rpm on a rotary shaker at room temperature for 68 h. Analysis by chiral HPLC reveals both S-CPIAm and the S-CPIA were produced from the R,S-CPIN.

| Time, h | mg nitrile | | mg amide | | mg acid | |
|---|---|---|---|---|---|---|
| | R-CPIN | S-CPIN | R-CPIAm | S-CPIAm | R-CPIA | S-CPIA |
| 0 | 9.6 | 9.6 | 0 | 0 | 0 | 0 |
| 68 | 9.6 | 8.4 | 0 | 0.84 | 0 | 0.42 |

EXAMPLE 17

Nucleotide sequencing of DNA regions flanking NRRL-18668 NHase gene

The nucleotide sequences of DNA regions flanking the NRRL-18668 NHase were determined by the Sanger dideoxy method (Sanger, F. (1981) Science 214:1205–1210) using double-stranded plasmid DNA as template. Using pSW1 (FIG. 1) as template, the nucleotide sequence downstream of NHase, down to the Xho1 site (FIG. 2), was determined. This sequence contains at least one gene, and potentially several more, which is defined as P14K, the nucleotide sequence of which is defined in Sequence Listing SEQ ID NO.:21, and the deduced amino acid sequence is defined in Sequence Listing SEQ ID NO.:22. P14K is required for NHase activity as described below.

The nucleotide sequence upstream of NHase, up to the EcoR1 (FIG. 2), was determined using pSW1 (FIG. 1) as template. The nucleotide sequence further upstream of the EcoR1 site was determined after subcloning DNA fragments corresponding to this region as follows. NRRL-18668 genomic DNA was digested with Pst1 and then self-ligated. Oligo-nucleotide primers designed to bind 3' to EcoR1 heading upstream (FIG. 2) and 5' to Pstl heading downstream (FIG. 2), and defined as Sequence Listing SEQ ID NO.:23 and Sequence Listing SEQ ID NO.:24, respectively, were used in a PCR reaction to amplify a 0.8 kb fragment corresponding to DNA upstream of the EcoR1 site (FIG. 8). NRRL-18668 genomic DNA was digested with EcoR1 and then self-ligated. Oligo-nucleotide primers designed to bind 3' to Pst1 heading upstream (FIG. 8) and 5' to EcoR1 heading downstream (FIG. 8), and defined as Sequence Listing SEQ ID NO.:25 and SEQ ID NO.:26, respectively, were used in a PCR reaction to amplify a 0.7 kb fragment corresponding to DNA upstream of the Pst1 site (FIG. 9). By subcloning and sequencing the PCR fragments, the nucleotide sequence upstream of NHase, up to the EcoR1 site (FIG. 9) was determined. This sequence contains at least one gene, and potentially more, which has been identified as encoding an amidase (based on homology to other amidase sequences), the nucleotide sequence of which is defined as Sequence Listing SEQ ID NO.:27, and the deduced amino acid sequence defined as Sequence Listing SEQ ID NO.:28.

A compiled map of the entire 8.0 kb DNA fragment, indicating genes identified, is shown in FIG. 10.

EXAMPLE 18

Construction of plasmids for expression of NRRL-18668 NHase in *Pichia pastoris*

The 0.9 kb EcoRl/Xbal fragment in pHIL-D4 (Phillips Petroleum, Bartlesville, Okla.) was replaced by the 0.9 kb EcoR1/Xba1 fragment from pAO815 (Invitrogen, San Diego, Calif.) to generate the plasmid pHIL-D4B2 (FIG. 11) which contains the following elements: 5'AOX1, *P. pastoris* methanol inducible alcohol oxidase I (AOX1) promoter; AOX1 term, *P. pastoris* AOX I transcriptional termination region; HIS4, *P. pastoris* histidinol dehydrogenase-encoding gene for selection in his4 hosts; kan, sequence derived from transposon Tn903 encoding aminoglycoside 3'-phosphotransferase, conferring kanamycin, neomycin and G418 resistance in a wide variety of hosts, and useful as an indicator of cassette copy number; 3'AOX1, *P. pastoris* sequence downstream from AOX1, used in conjunction with 5'AOX1 for site-directed vector integration; ori, pBR322 origin of DNA replication allowing plasmid manipulations in *E. coli*; and amp, β-lactamase gene from pBR322 conferring resistance to ampicillin. An additional feature of PHIL-D4B2 is that multiple expression cassettes (5'AOX1-gene-AOX1term) can easily be placed into one plasmid by subcloning cassettes on Bgl2/Xba1 fragments into BamH1/Xba1 sites.

The genes encoding α, β, and P14K (FIG. 10) were PCR amplified using primers with EcoR1 sites at the 5' ends. The PCR products were digested with EcoR1, and subcloned into the EcoR1 site of pHIL-D4B2 to generate pSW46 (FIG. 12), pSW47 (FIG. 13) and pSW48 (FIG. 14), respectively. The Bgl2/Xba1 fragment from pSW47 containing the β expression cassette was subcloned into the BamH1/Xba1 sites of pSW46 to generate pSW49 (FIG. 15), which contains expression cassettes for α and β. The Bgl2/Xba1 fragment from pSW48 containing the P14K expression cassette was subcloned into the BamH1/Xba1 sites of pSW49 to generate pSW50 (FIG. 16), which contains expression cassettes for α, β and P14K.

EXAMPLE 19

Construction of *Pichia pastoris* strain for expression of NRRL-18668 NHase

*P. pastoris* strain GTS115(his4) (Phillips Petroleum, Bartlesville, Okla.) was transformed with 1–2 μg of Bgl2-linearized plasmid pSW49 or 1–2 μg of Bgl2-linearized plasmid pSW50 using the spheroplast transformation method as described (Cregg et al. (1985) *Mol. Cell. Biol.* 5: 3376–3385). Cells were regenerated on plates without histidine for 3–4 d at 30° C. All transformants arise after integration of plasmid DNA into the chromosome. Chromosomal DNA was prepared from his$^+$ transformants and subjected to PCR analysis with primers specific for α, β and P14K genes. An isolated pSW49 transformant positive for α and β genes, and an isolated pSW50 transformant positive for α, β and P14K genes, designated SW49 and SW50.2, respectively, were selected for further study. *P. pastoris* strain SW50.2 was deposited with ATCC and assigned accession number ATCC 74391.

EXAMPLE 20

NRRL-18668 NHase activity in engineered *P. pastoris*

*P. pastoris* strains SW49 and SW50.2 were grown to $A_{600}$ of 2–10 in MGY (1.34% yeast nitrogen base without amino acids, 0.00004% biotin, 1% glycerol) with shaking at 30° C. Cells are then pelleted and induced by resuspending in MM (1.34% yeast nitrogen base without amino acids, 0.00004% biotin, 0.5% methanol) and incubated with shaking at 30° C. for 1–4 d. Cells were harvested by centrifugation and washed in PBS (0.1M $KH_2PO_4$, pH 7.2). NHase activity was demonstrated by methacrylonitrile assay, in which cells were resuspended in PBS at $A_{600}$ of 0.6, and methacrylonitrile was added to a final concentration of 10 mM. After incubation with shaking at room temperature, conversion of methacrylonitrile to methacrylamide by NHase was demonstrated by monitoring the increase in $A_{224}$ of the supernatant. Cells boiled before assay serve as a negative control. NHase activity was observed in SW50.2 which harbors expression cassettes for α, β and P14K, while SW49, which only harbors expression cassettes for α and β showed negligible NHase activity.

| | $A_{224}$ | | |
|---|---|---|---|
| rxn time, min | SW49 | SW50.2 | SW50.2 boil |
| 0 | 0.260 | 0.360 | 0.110 |
| 15 | 0.360 | 1.390 | 0.125 |

Stereospecific NHase activity was also demonstrated in induced SW50.2 cells by using R-2-(4-chlorophenyl)-3-methylbutyronitrile (R-CPIN) or S-2-(4-chlorophenyl)-3-methylbutyronitrile (S-CPIN) as substrate and and then analyzing for conversion to the corresponding amides (R-CPIAm and S-CPIAm, respectively) by HPLC.

| | mM | | | |
|---|---|---|---|---|
| rxn time, h | R-CPIN | R-CPIAm | S-CPIN | S-CPIAm |
| 0 | 10 | 0 | 10 | 0 |
| 48 | 10 | 0 | 5.5 | 4.5 |

Bioconversion of adiponitrile (ADN) to 5-cyanovaleramide (5-CVAm) was also demonstrated in permeabilized SW50.2 cells, and in SW50.2 cell extracts. Permeabilized cells were prepared by the addition of benzalkonium chloride (Lonza Baequat MB-50) to a 10% (wt) suspension of induced cells to yeild 1% (wt MB-50:wt cells). The suspension was then mixed on a nutator mixer for 60 min at room temperature, after which cells were washed by centrifugation 3 times with 50 mM phospahte buffer, pH 7.0. Extracts were prepared by rapidly vortexing induced cells with 0.5 mm glass beads (BioSpec Products) in 50 mM $KH_2PO_4$, pH 7.0/1 mM EDTA/0.1 mM PMSF for 2 min. NHase activity was determined to be 34–38 U/g wet wt (permeabilized cells), and 35-56 U/g wet wt (cell extracts).

EXAMPLE 21

Construction of plasmid for expression of NRRL-18668 amidase in *E. coli*

The gene encoding NRRL-18688 amidase was PCR amplified using an upstream primer with a Hind3 site at the 5' end and a downstream primer with an Xho1 site at the 5' end. The PCR product was subcloned into the vector pET-21a(+) (Novagen, Madison, Wis.) between the Hind3 and Xho1 sites to generate the expression plasmid pSW37 (FIG. 17).

EXAMPLE 22

Construction of *E. coli* strain for expression of NRRL-18668 amidase

*E. coli* strain BL21(DE3) (Novagen, Madison, Wis.) was transformed with pSW37 using the calcium chloride procedure (Maniatis et al. (1989) Molecular Cloning: A Laboratory Manual), and an isolated transformant was designated SW37, and deposited with ATCC and assigned accession number ATCC 98174. Induced SW37 shows production of amidase enzyme based on Coomassie Blue stained denaturing polyacrylamide gel electrophoresis of soluble cell extract.

EXAMPLE 23

NRRL-18668 amidase activity in engineered *E. coli*

*E. coli* strain SW37 is grown in LB media at 30° C. to $A_{600}$=0.5, at which time IPTG is added to 1 mM and incubation continued for 2 h. Cells are then pelleted and washed in PBS. Cells are incubated with 10 mM butyramide and conversion to butyric acid is monitored by HPLC.

EXAMPLE 24

Construction of plasmid for expression of NRRL-18668 amidase and NHase in *E. coli*

The entire 8.0 kb DNA fragment (shown in FIG. 10) was subcloned between the EcoR1 and Xho1 sites of the vector pET-21(+) (Novagen, Madison, Wis.) to generate the plasmid pSW23 (FIG. 18).

EXAMPLE 25

Construction of *E. coli* strain for co-expression of NRRL-18668 amidase and NHase

*E. coli* strain BL21(DE3) (Novagen, Madison, Wis.) was transformed with pSW23 using the calcium chloride procedure (Maniatis et al. (1989) Molecular Cloning: A Laboratory Manual), and an isolated transformant was designated SW23, and deposited with ATCC and assigned accession number ATCC 98175. Induced SW23 shows production of NHase enzyme and amidase enzyme based on Coomassie Blue stained denaturing polyacrylamide gel electrophoresis of soluble cell extract.

EXAMPLE 26

NRRL-18668 amidase and NHase activity in engineered *E. coli*

*E. coli* strain SW23 is grown in LB media at 30° C. to $A_{600}$=0.5, at which time IPTG is added to 1 mM and incubation continued for 2 h. Cells are then pelleted and washed in PBS. Cells are incubated with 10 mM butyronitrile and conversion to butyric acid is monitored by HPLC. Stereospecific conversion of S-CPIN, relative to R-CPIN, to the corresponding acid (S-CPIAc) can also be monitored by HPLC.

What is claimed is:

1. A method for converting a nitrile of the formula $$A-\underset{\underset{R^2}{|}}{\overset{\overset{R^1}{|}}{C}}-CN$$

I (R,S)

wherein:

A is selected from the group consisting of:

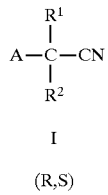

A-1, A-2

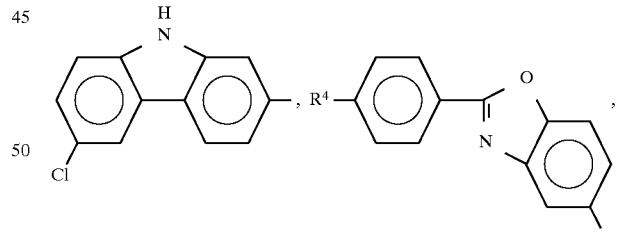

A-3, A-4

-continued

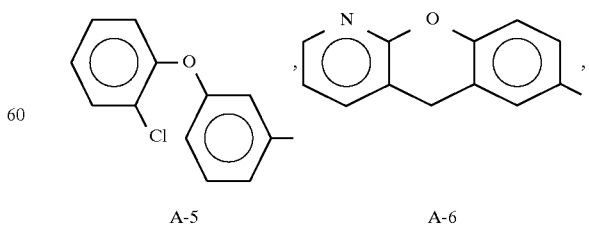

A-5, A-6

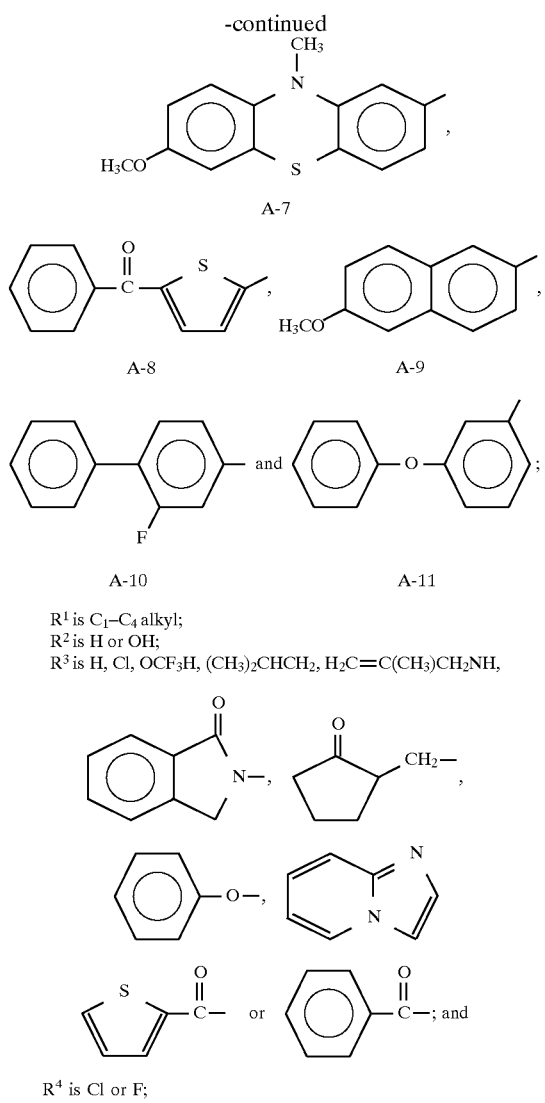

R[1] is $C_1$–$C_4$ alkyl;
R[2] is H or OH;
R[3] is H, Cl, $OCF_2H$, $(CH_3)_2CHCH_2$, $H_2C=C(CH_3)CH_2NH$,

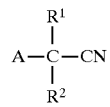

R[4] is Cl or F;

to the corresponding amide comprising 1) contacting said nitrile with the transformed host cell comprising a nucleic acid fragment having the nucleotide sequence represented by SEQ ID NO.:17 that stereospecifically converts the racemic nitrile to the corresponding enantiomeric R- or S-amide, the host cell selected from the group consisting of Escherichia, Pseudomonas, Rhodococcus, Acinetobacter, Bacillus, Streptomyces, Hansenula, Saccharomyces, Pichia, Aspergillus, Neurospora, and Penicillium, 2) recovering the product of Step 1).

2. A method for converting a nitrile of the formula $$A-\underset{R^2}{\overset{R^1}{\underset{|}{\overset{|}{C}}}}-CN$$

I (R,S)

wherein:

A is selected from the group consisting of:

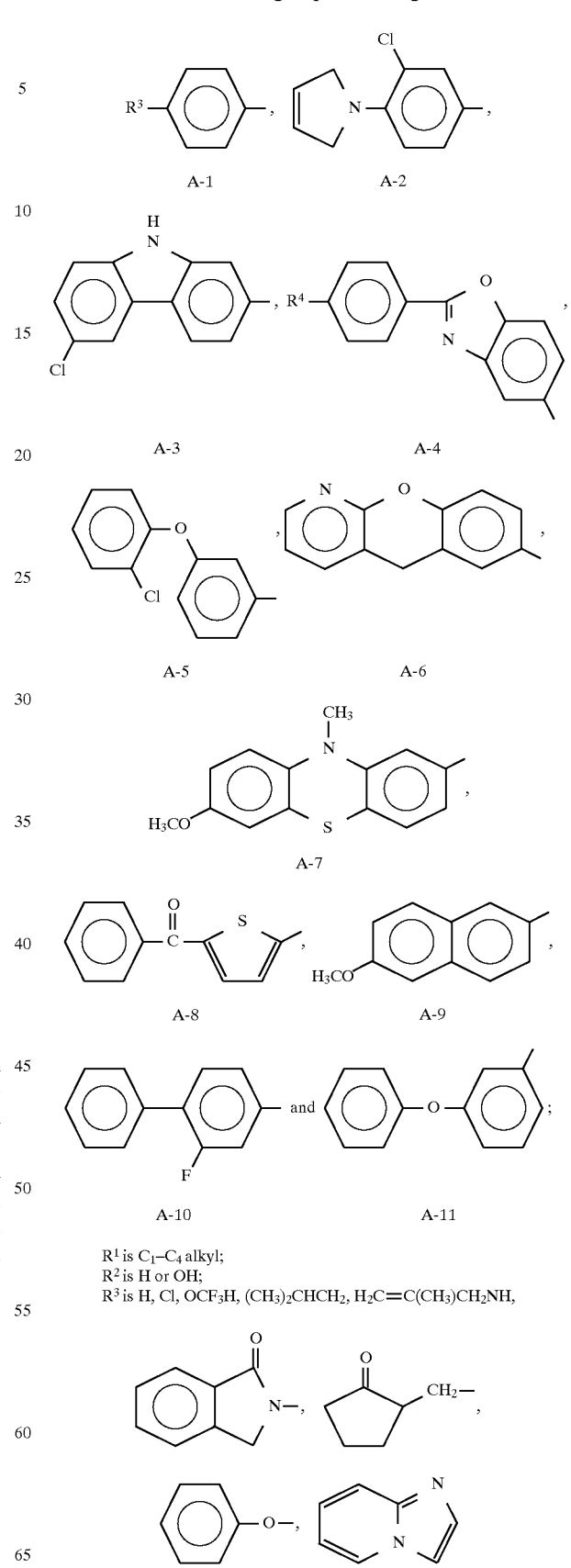

R[1] is $C_1$–$C_4$ alkyl;
R[2] is H or OH;
R[3] is H, Cl, $OCF_2H$, $(CH_3)_2CHCH_2$, $H_2C=C(CH_3)CH_2NH$,

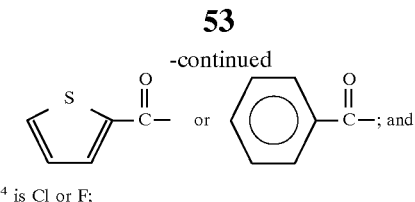

$R^4$ is Cl or F;

to the corresponding enantiomeric (R) or (S)-carboxylic acid comprising 1) contacting the nitrile with the transformed host that comprises a 5.0 kb EcoR1/Hind3 fragment of a 6.5 kb nucleic acid fragment as characterized by the restriction map shown in FIG. 2 and a nucleic acid fragment having the sequence of SEQ ID NO:20, wherein said host stereospecifically converts the racemic nitrile to the corresponding enantiomeric (R)- or (S)-carboxylic acid, the host cell selected from the group consisting of Escherichia, Pseudomonas, Rhodococcus, Acinetobacter, Bacillus, Streptomyces, Hansenula, Saccharomyces, Pichia, Aspergillus, Neurospora, and Penicillium, and 2) recovering the product of Step 1).

3. A method for converting a nitrile of the formula

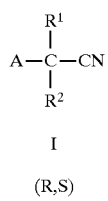

I (R,S)

wherein:

A is selected from the group consisting of:

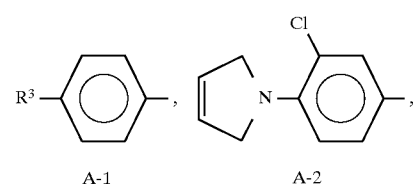

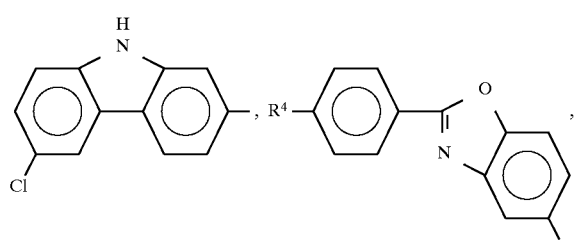

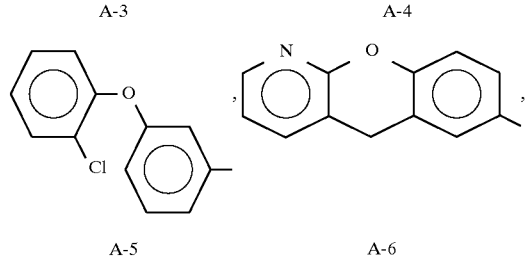

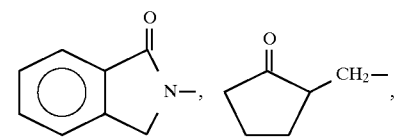

$R^1$ is $C_1-C_4$ alkyl;
$R^2$ is H or OH;
$R^3$ is H, Cl, $OCF_3H$, $(CH_3)_2CHCH_2$, $H_2C=C(CH_3)CH_2NH$,

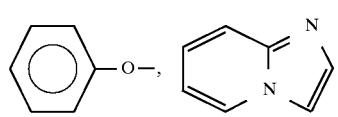

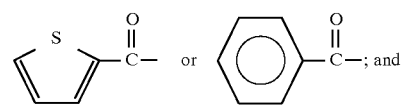

$R^4$ is Cl or F;

to the corresponding amide comprising 1) contacting said nitrile with a transformed host cell comprising the nucleic acid fragment having the sequence of SEQ ID NO:17 and the nucleic acid frogment corresponding to the P14K region of a 6.5 kb nucleic acid fragment as shown in FIG. 10 wherein said fragment encodes a polypeptide having an aminp acis sequence of SEQ ID NO:22 the host cell capable of stereospecifically converting the racemic nitrile to the corresponding enantiomeric R- or S-amide, the host cell selected from the group consisting of Escherichia, Pseudomonas, Rhodococcus, Acinetobacter, Bacillus, Streptomyces, Hansenula, Saccharomyces, Pichia, Aspergillus, Neurospora, and Penicillium, 2) recovering the product of Step 1).

4. A method for converting a nitrile of the formula

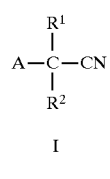

(R,S)

wherein:

A is selected from the group consisting of:

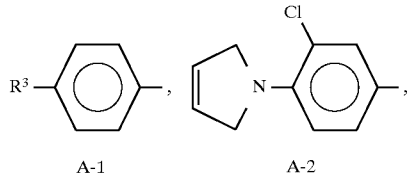

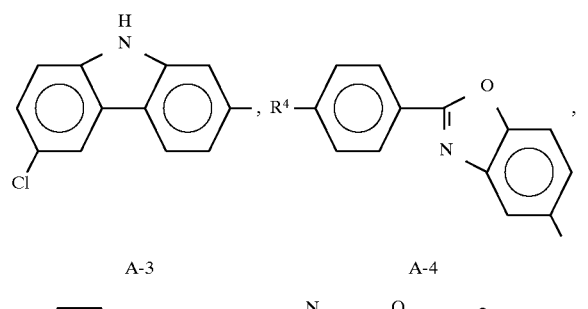

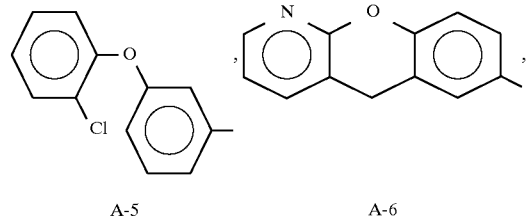

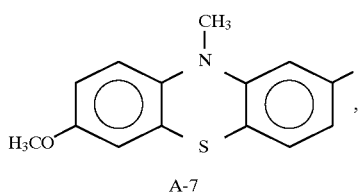

$R^1$ is $C_1$–$C_4$ alkyl;
$R^2$ is H or OH;
$R^3$ is H, Cl, OCF$_3$H, (CH$_3$)$_2$CHCH$_2$, H$_2$C=C(CH$_3$)CH$_2$NH, $R^4$ is Cl or F;

to the corresponding enantiomeric (R) or (S)-carboxylic acid comprising 1) contacting the nitrile with the transformed *Pichia pastoris* comprising pSW50 and identified as ATCC 74391 that stereospecifically converts the racemic nitrile to the corresponding enantiomeric (R)- or (S)-carboxylic acid, the host cell selected from the group consisting of Escherichia, Pseudomonas, Rhodococcus, Acinetobacter, Bacillus, Streptomyces, Hansenula, Saccharomyces, Pichia, Aspergillus, Neurospora, and Penicillium, and 2) recovering the product of Step 1).

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 210 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: No ( x i ) SEQUENCE DESCRIPTION: SEQ ID NO: 1:

```
Met Gly Gln Ser His Thr His Asp His His His Asp Gly Tyr Gln Ala
1               5                   10                  15

Pro Pro Glu Asp Ile Ala Leu Arg Val Lys Ala Leu Glu Ser Leu Leu
                20              25                  30

Ile Glu Lys Gly Leu Val Asp Pro Ala Ala Met Asp Leu Val Val Gln
            35              40                  45

Thr Tyr Glu His Lys Val Gly Pro Arg Asn Gly Ala Lys Val Val Ala
        50              55                  60

Lys Ala Trp Val Asp Pro Ala Tyr Lys Ala Arg Leu Leu Ala Asp Ala
65                      70                  75                  80

Thr Ala Ala Ile Ala Glu Leu Gly Phe Ser Gly Val Gln Gly Glu Asp
                85                  90                  95

Met Val Ile Leu Glu Asn Thr Pro Ala Val His Asn Val Phe Val Cys
            100                 105                 110

Thr Leu Cys Ser Cys Tyr Pro Trp Pro Thr Leu Gly Leu Pro Pro Ala
        115                 120                 125

Trp Tyr Lys Ala Ala Ala Tyr Arg Ser Arg Met Val Ser Asp Pro Arg
    130                 135                 140

Gly Val Leu Ala Glu Phe Gly Leu Val Ile Pro Ala Asn Lys Glu Ile
145                 150                 155                 160

Arg Val Trp Asp Thr Thr Ala Glu Leu Arg Tyr Met Val Leu Pro Glu
                165                 170                 175

Arg Pro Gly Thr Glu Ala Tyr Ser Glu Glu Gln Leu Ala Glu Leu Val
            180                 185                 190

Thr Arg Asp Ser Met Ile Gly Thr Gly Leu Pro Thr Gln Pro Thr Pro
        195                 200                 205

Ser His
    210
```

( 2 ) INFORMATION FOR SEQ ID NO:2:

( i ) SEQUENCE CHARACTERISTICS:
        ( A ) LENGTH: 217 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: No ( x i ) SEQUENCE DESCRIPTION: SEQ ID NO: 2:

```
Met Asn Gly Ile His Asp Thr Gly Gly Ala His Gly Tyr Gly Pro Val
```

```
          1                   5                        10                        15
Tyr   Arg   Glu   Pro   Asn   Glu   Pro   Val   Phe   Arg   Tyr   Asp   Trp   Glu   Lys   Thr
                  20                      25                      30

Val   Met   Ser   Leu   Leu   Pro   Ala   Leu   Leu   Ala   Asn   Ala   Asn   Phe   Asn   Leu
            35                      40                            45

Asp   Glu   Phe   Arg   His   Ser   Ile   Glu   Arg   Met   Gly   Pro   Ala   His   Tyr   Leu
      50                            55                            60

Glu   Gly   Thr   Tyr   Tyr   Glu   His   Trp   Leu   His   Val   Phe   Glu   Asn   Leu   Leu
65                            70                      75                                  80

Val   Glu   Lys   Gly   Val   Leu   Thr   Ala   Thr   Glu   Val   Ala   Thr   Gly   Lys   Ala
                        85                            90                            95

Ala   Ser   Gly   Lys   Thr   Ala   Thr   Arg   Val   Leu   Thr   Pro   Ala   Ile   Val   Asp
                  100                       105                             110

Asp   Ser   Ser   Ala   Pro   Gly   Leu   Leu   Arg   Pro   Gly   Gly   Gly   Phe   Ser   Phe
            115                           120                         125

Phe   Pro   Val   Gly   Asp   Lys   Val   Arg   Val   Leu   Asn   Lys   Asn   Pro   Val   Gly
      130                             135                       140

His   Thr   Arg   Met   Pro   Arg   Tyr   Thr   Arg   Ala   Lys   Trp   Gly   Gln   Trp   Ser
145                             150                       155                             160

Ser   Thr   Met   Val   Cys   Phe   Val   Thr   Pro   Asp   Thr   Ala   Ala   His   Gly   Lys
                        165                             170                       175

Gly   Glu   Gln   Pro   Gln   His   Val   Tyr   Thr   Val   Ser   Phe   Thr   Ser   Val   Glu
                  180                             185                       190

Leu   Trp   Gly   Gln   Asp   Ala   Ser   Ser   Pro   Lys   Asp   Thr   Ile   Arg   Val   Asp
            195                             200                       205

Leu   Trp   Asp   Asp   Tyr   Leu   Glu   Pro   Ala
210                             215
```

( 2 ) INFORMATION FOR SEQ ID NO:3:

( i ) SEQUENCE CHARACTERISTICS:
        ( A ) LENGTH: 633 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: No ( x i ) SEQUENCE DESCRIPTION: SEQ ID NO: 3:

```
ATGGGGCAAT   CACACACGCA   TGACCACCAT   CACGACGGGT   ACCAGGCACC   GCCCGAAGAC      60
ATCGCGCTGC   GGGTCAAGGC   CTTGGAGTCT   CTGCTGATCG   AGAAGGTCT    TGTCGACCCA     120
GCGGCCATGG   ACTTGGTCGT   CCAAACGTAT   GAACACAAGG   TAGGCCCCCG   AAACGGCGCC     180
AAAGTCGTGG   CCAAGGCCTG   GGTGGACCCT   GCCTACAAGG   CCCGTCTGCT   GGCAGACGCA     240
ACTGCGGCAA   TTGCCGAGCT   GGGCTTCTCC   GGGGTACAGG   GCGAGGACAT   GGTCATTCTG     300
GAAAACACCC   CCGCCGTCCA   CAACGTCTTC   GTTTGCACCT   TGTGCTCTTG   CTACCCATGG     360
CCGACGCTGG   GCTTGCCCCC   TGCCTGGTAC   AAGGCCGCCG   CCTACCGGTC   CGCATGGTG      420
AGCGACCCGC   GTGGGGTTCT   CGCGGAGTTC   GGCCTGGTGA   TCCCCGCCAA   CAAGGAAATC     480
CGCGTCTGGG   ACACCACGGC   CGAATTGCGC   TACATGGTGC   TGCCGGAACG   GCCCGGAACT     540
GAAGCCTACA   GCGAAGAACA   ACTGGCCGAA   CTCGTTACCC   GCGATTCGAT   GATCGGCACC     600
GGCCTGCCAA   CCCAACCCAC   CCCATCTCAT   TAA                                     633
```

( 2 ) INFORMATION FOR SEQ ID NO:4:

( i ) SEQUENCE CHARACTERISTICS:
    ( A ) LENGTH: 654 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: No ( x i ) SEQUENCE DESCRIPTION: SEQ ID NO: 4:

```
ATGAATGGCA  TTCACGATAC  TGGCGGAGCA  CATGGTTATG  GGCCGGTTTA  CAGAGAACCG      60
AACGAACCCG  TCTTTCGCTA  CGACTGGGAA  AAAACGGTCA  TGTCCCTGCT  CCCGGCCCTG     120
CTCGCCAACG  CGAACTTCAA  CCTCGATGAA  TTTCGGCATT  CGATCGAGCG  AATGGGCCCG     180
GCCCACTATC  TGGAGGGAAC  CTACTACGAA  CACTGGCTTC  ATGTCTTTGA  GAACCTGCTG     240
GTCGAGAAGG  GTGTGCTCAC  GGCCACGGAA  GTCGCGACCG  GCAAGGCTGC  GTCTGGCAAG     300
ACGGCGACGC  GCGTGCTGAC  GCCGGCCATC  GTGGACGACT  CGTCAGCACC  GGGGCTTCTG     360
CGCCCGGGAG  GAGGGTTCTC  TTTTTTTCCT  GTGGGGACA   AGGTTCGCGT  CCTCAACAAG     420
AACCCGGTGG  GCCATACCCG  CATGCCGCGC  TACACGCGGG  CAAAGTGGGG  ACAGTGGTCA     480
TCGACCATGG  TGTGTTTCGT  GACGCCGGAC  ACCGCGGCAC  ACGGAAAGGG  CGAGCAGCCC     540
CAGCACGTTT  ACACCGTGAG  TTTCACGTCG  GTCGAACTGT  GGGGGCAAGA  CGCTTCCTCG     600
CCGAAGGACA  CGATTCGCGT  CGACTTGTGG  GATGACTACC  TGGAGCCAGC  GTGA           654
```

( 2 ) INFORMATION FOR SEQ ID NO:5:

( i ) SEQUENCE CHARACTERISTICS:
        ( A ) LENGTH: 30 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: No ( x i ) SEQUENCE DESCRIPTION: SEQ ID NO: 5:

```
Gly Gln Ser His Thr His Asp His His His Asp Gly Tyr Gln Ala Pro
 1               5                  10                  15
Pro Glu Asp Ile Ala Leu Arg Val Lys Ala Leu Glu Ser Leu
20                  25                  30
```

( 2 ) INFORMATION FOR SEQ ID NO:6:

( i ) SEQUENCE CHARACTERISTICS:
        ( A ) LENGTH: 13 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: No ( x i ) SEQUENCE DESCRIPTION: SEQ ID NO: 6:

```
Asp Leu Val Val Gln Thr Tyr Glu His Lys Val Gly Pro
 1               5                  10
```

( 2 ) INFORMATION FOR SEQ ID NO:7:

( i ) SEQUENCE CHARACTERISTICS:
        ( A ) LENGTH: 16 amino acids
        ( B ) TYPE: amino acid (C) STRANDEDNESS: unknown
            (D) TOPOLOGY: unknown (ii) MOLECULE TYPE: peptide (iii) HYPOTHETICAL: No (xi) SEQUENCE DESCRIPTION: SEQ ID NO: 7:

Asn Gly Ala Lys Val Val Ala Lys Ala Trp Val Asp Pro Ala Tyr Lys
1               5                   10                  15

(2) INFORMATION FOR SEQ ID NO:8:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (iii) HYPOTHETICAL: No (xi) SEQUENCE DESCRIPTION: SEQ ID NO: 8:

Asp Pro Arg Gly Val Leu Ala Glu Phe Gly
1               5                   10

(2) INFORMATION FOR SEQ ID NO:9:

(i) SEQUENCE CHARACTERISTICS:
            (A) LENGTH: 10 amino acids
            (B) TYPE: amino acid
            (C) STRANDEDNESS: unknown
            (D) TOPOLOGY: unknown (ii) MOLECULE TYPE: peptide (iii) HYPOTHETICAL: No (xi) SEQUENCE DESCRIPTION: SEQ ID NO: 9:

Gly Leu Pro Thr Gln Pro Thr Pro Ser His
1               5                   10

(2) INFORMATION FOR SEQ ID NO:10:

(i) SEQUENCE CHARACTERISTICS:
            (A) LENGTH: 83 amino acids
            (B) TYPE: amino acid
            (C) STRANDEDNESS: unknown
            (D) TOPOLOGY: unknown (ii) MOLECULE TYPE: protein (iii) HYPOTHETICAL: No (xi) SEQUENCE DESCRIPTION: SEQ ID NO: 10:

Met Asn Gly Ile His Asp Thr Gly Gly Ala His Gly Tyr Gly Pro Val
1               5                   10                  15

Tyr Arg Glu Pro Asn Glu Pro Val Phe Arg Tyr Asp Trp Glu Lys Thr
                20                  25                  30

Val Met Ser Leu Leu Pro Ala Leu Xaa Ala Asn Gly Asn Phe Asn Leu
                35                  40                  45

Asp Glu Phe Arg His Ser Ile Glu Arg Met Gly Pro Ala His Tyr Leu
                50                  55                  60

Glu Gly Thr Tyr Tyr Glu His Trp Leu His Val Phe Glu Asn Leu Leu
65                  70                  75                  80

Val Glu Lys ( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: No ( x i ) SEQUENCE DESCRIPTION: SEQ ID NO: 11:

```
Gly Glu His Pro Gln His Val Tyr
1               5
```

( 2 ) INFORMATION FOR SEQ ID NO:12:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: No ( x i ) SEQUENCE DESCRIPTION: SEQ ID NO: 12:

```
Ser Phe Thr Ser Val Glu Leu Trp Gly Gln Asp Ala Ser Ser Pro Lys
1               5                   1 0                 1 5
```

( 2 ) INFORMATION FOR SEQ ID NO:13:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: unknown ( i i ) MOLECULE TYPE: peptide ( i i i ) HYPOTHETICAL: No ( x i ) SEQUENCE DESCRIPTION: SEQ ID NO: 13:

```
Val Asp Leu Trp Asp Asp Tyr Leu Glu Pro Ala
1               5                   1 0
```

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: No ( x i ) SEQUENCE DESCRIPTION: SEQ ID NO: 14:

```
GGAATTCGAY  CAYCAYCAYG  A                                              2 1
```

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (ii) MOLECULE TYPE: DNA (genomic)

(iii) HYPOTHETICAL: No (xi) SEQUENCE DESCRIPTION: SEQ ID NO: 15:

| | |
|---|---|
| GGAATTCTTY TCCCARTCRT A | 21 |

(2) INFORMATION FOR SEQ ID NO:16:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: No (xi) SEQUENCE DESCRIPTION: SEQ ID NO: 16:

| | | | | | | |
|---|---|---|---|---|---|---|
| GAATTCGATC | ACCATCACGA | CGGGTACCAG | GCACCGCCCG | AAGACATCGC | GCTGCGGGTC | 60 |
| AAGGCCTTGG | AGTCTCTGCT | GATCGAGAAA | GGTCTTGTCG | ACCCAGCGGC | CATGGACTTG | 120 |
| GTCGTCCAAA | CGTATGAACA | CAAGGTAGGC | CCCCGAAACG | GCGCCAAAGT | CGTGGCCAAG | 180 |
| GCCTGGGTGG | ACCCTGCCTA | CAAGGCCCGT | CTGCTGGCAG | ACGCAACTGC | GGCAATTGCC | 240 |
| GAGCTGGGCT | TCTCCGGGGT | ACAGGGCGAG | GACATGGTCA | TTCTGGAAAA | CACCCCCGCC | 300 |
| GTCCACAACG | TCTTCGTTTG | CACCTTGTGC | TCTTGCTACC | CATGGCCGAC | GCTGGGCTTG | 360 |
| CCCCCTGCCT | GGTACAAGGC | CGCCGCCTAC | CGGTCCCGCA | TGGTGAGCGA | CCCGCGTGGG | 420 |
| GTTCTCGCGG | AGTTCGGCCT | GGTGATCCCC | GCCAACAAGG | AAATCCGCGT | CTGGGACACC | 480 |
| ACGGCCGAAT | TGCGCTACAT | GGTGCTGCCG | GAACGGCCCG | GAACTGAAGC | CTACAGCGAA | 540 |
| GAACAACTGG | CCGAACTCGT | TACCCGCGAT | TCGATGATCG | GCACCGGCCT | GCCAACCCAA | 600 |
| CCCACCCCAT | CTCATTAAGG | AGTTCGTCAT | GAATGGCATT | CACGATACTG | GCGGAGCACA | 660 |
| TGGTTATGGG | CCGGTTTACA | GAGAACCGAA | CGAACCCGTC | TTTCGCTACG | ACTGGGAAAA | 720 |
| GAATTC | | | | | | 726 |

(2) INFORMATION FOR SEQ ID NO:17:

(i) SEQUENCE CHARACTERISTICS:
        (A) LENGTH: 1440 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: No (xi) SEQUENCE DESCRIPTION: SEQ ID NO: 17:

| | | | | | | |
|---|---|---|---|---|---|---|
| CGGGAGCGCA | ATCTGCAAGG | TGGCATTGGC | CTTCAGTGTC | GATGCCGAGT | TGAAGTCGCT | 60 |
| GTACCCCTTT | TTTCAACCAC | ACCAGGAGAA | CCGCACCATG | GGGCAATCAC | ACACGCATGA | 120 |
| CCACCATCAC | GACGGGTACC | AGGCACCGCC | CGAAGACATC | GCGCTGCGGG | TCAAGGCCTT | 180 |
| GGAGTCTCTG | CTGATCGAGA | AAGGTCTTGT | CGACCCAGCG | GCCATGGACT | TGGTCGTCCA | 240 |
| AACGTATGAA | CACAAGGTAG | GCCCCCGAAA | CGGCGCCAAA | GTCGTGGCCA | AGGCCTGGGT | 300 |
| GGACCCTGCC | TACAAGGCCC | GTCTGCTGGC | AGACGCAACT | GCGGCAATTG | CCGAGCTGGG | 360 |
| CTTCTCCGGG | GTACAGGGCG | AGGACATGGT | CATTCTGGAA | AACACCCCCG | CCGTCCACAA | 420 |
| CGTCTTCGTT | TGCACCTTGT | GCTCTTGCTA | CCCATGGCCG | ACGCTGGGCT | TGCCCCCTGC | 480 |

| | | | | | | |
|---|---|---|---|---|---|---|
|CTGGTACAAG|GCCGCCGCCT|ACCGGTCCCG|CATGGTGAGC|GACCCGCGTG|GGGTTCTCGC|540|
|GGAGTTCGGC|CTGGTGATCC|CCGCCAACAA|GGAAATCCGC|GTCTGGGACA|CCACGGCCGA|600|
|ATTGCGCTAC|ATGGTGCTGC|CGGAACGGCC|CGGAACTGAA|GCCTACAGCG|AAGAACAACT|660|
|GGCCGAACTC|GTTACCCGCG|ATTCGATGAT|CGGCACCGGC|CTGCCAACCC|AACCCACCCC|720|
|ATCTCATTAA|GGAGTTCGTC|ATGAATGGCA|TTCACGATAC|TGGCGGAGCA|CATGGTTATG|780|
|GGCCGGTTTA|CAGAGAACCG|AACGAACCCG|TCTTTCGCTA|CGACTGGGAA|AAAACGGTCA|840|
|TGTCCCTGCT|CCCGGCCCTG|CTCGCCAACG|CGAACTTCAA|CCTCGATGAA|TTTCGGCATT|900|
|CGATCGAGCG|AATGGGCCCG|GCCCACTATC|TGGAGGGAAC|CTACTACGAA|CACTGGCTTC|960|
|ATGTCTTTGA|GAACCTGCTG|GTCGAGAAGG|GTGTGCTCAC|GGCCACGGAA|GTCGCGACCG|1020|
|GCAAGGCTGC|GTCTGGCAAG|ACGGCGACGC|GCGTGCTGAC|GCCGGCCATC|GTGGACGACT|1080|
|CGTCAGCACC|GGGGCTTCTG|CGCCCGGGAG|GAGGGTTCTC|TTTTTTTCCT|GTGGGGACA|1140|
|AGGTTCGCGT|CCTCAACAAG|AACCCGGTGG|GCCATACCCG|CATGCCGCGC|TACACGCGGG|1200|
|CAAAGTGGGG|ACAGTGGTCA|TCGACCATGG|TGTGTTTCGT|GACGCCGGAC|ACCGCGGCAC|1260|
|ACGGAAAGGG|CGAGCAGCCC|CAGCACGTTT|ACACCGTGAG|TTTCACGTCG|GTCGAACTGT|1320|
|GGGGGCAAGA|CGCTTCCTCG|CCGAAGGACA|CGATTCGCGT|CGACTTGTGG|GATGACTACC|1380|
|TGGAGCCAGC|GTGATCATGA|AAGACGAACG|GTTTCCATTG|CCAGAGGGTT|CGCTGAAGGA|1440|

( 2 ) INFORMATION FOR SEQ ID NO:18:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: No ( x i ) SEQUENCE DESCRIPTION: SEQ ID NO: 18:

| | | | |
|---|---|---|---|
|GAGGAATTCA|TGGCCATTAC|TCGCCCTACC C|31|

( 2 ) INFORMATION FOR SEQ ID NO:19:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: No ( x i ) SEQUENCE DESCRIPTION: SEQ ID NO: 19:

| | | | |
|---|---|---|---|
|GTCGAATTCT|CAGAGCGTGC|GCCAGTCCAC C|31|

( 2 ) INFORMATION FOR SEQ ID NO:20:

( i ) SEQUENCE CHARACTERISTICS:
        ( A ) LENGTH: 1521 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: No ( x i ) SEQUENCE DESCRIPTION: SEQ ID NO: 20:

```
ATGGCCATTA CTCGCCCTAC CCTCGACCAG GTTTTAGACA TCCGAACCCA GTTGCACATG      60

CAACTGACGC ACGAACAGGC AGCGTCCTAC CTGGAACTGA TGCAACCGAG TTTCGACGCC     120

TACGACCTGG TCGACGAACT GGCTGATTTC GTTCCGCCAA TACGCTACGA CCGCAGTTCA     180

GGCTATCGCC ATCGGCCATC GGCCAAGGAA AACCCTCTGA ACGCCTGGTA CTACCGAACA     240

GAAGTGAATG GTGCCCGCGA AGGCCTGCTG GCGGGCAAAA CCGTCGCGCT CAAAGATAAT     300

ATCTCCCTGG CAGGCGTCCC CATGATGAAC GGCGCAGCGC CGTTGGAAGG CTTCGTCCCG     360

GGGTTCGATG CCACGGTGGT CACCCGCTTG CTCGATGCGG GGGCGACCAT TCTCGGCAAA     420

GCCACCTGCG AGCACTACTG CCTTTCAGGA GGCAGCCACA CCTCCGATCC AGCCCCGGTG     480

CACAACCCAC ATCGCCACGG TTATGCCTCT GGCGGTTCCT CATCAGGCAG CGCGGCATTG     540

GTTGCGTCCG GTGAGGTGGA CATCGCCGTG GGCGGCGATC AAGGCGGCTC CATTCGGATC     600

CCGTCGGCCT TCTGCGGTAC CTACGGCATG AAGCCCACCC ACGGCCTGGT GCCCTACACC     660

GGCGTCATGG CGATTGAAGC CACGATCGAT CATGTCGGCC CCATCACCGG TAACGTGCGC     720

GACAACGCGC TGATGCTGCA GGCAATGGCC GGTGCAGACG GACTCGACCC GCGCCAGGCG     780

GCGCCTCAGG TCGATGACTA TTGCAGTTAC CTGGAAAAAG GCGTGAGCGG ACTCAGAATC     840

GGGGTGTTGC AAGAGGGATT CGCGCTTGCT AACCAGGACC CTCGCGTGGC GGACAAAGTG     900

CGCGACGCCA TCGCCCGACT CGAGGCGTTG GGCGCTCATG TCGAGCCGGT CTCCATTCCC     960

GAGCACAACC TGGCAGGGTT GTTGTGGCAC CCCATCGGTT GCGAAGGCTT GACCATGCAG    1020

ATGATGCATG GCAACGGCGC AGGCTTTAAC TGGAAAGGAC TTTACGATGT CGGCCTGCTG    1080

GACAAACAAG CCAGCTGGCG CGACGACGCA GACCAATTAT CCGCGTCGCT CAAGCTCTGC    1140

ATGTTCGTCG GCCAATACGG CCTGTCGCGC TACAACGGAC GCTACTACGC CAAGGCCCAG    1200

AACCTTGCAC GCTTTGCCCG GCAGGGATAC GACAAAGCGC TGCAAACCTA TGACCTGCTG    1260

GTGATGCCGA CCACGCCCAT CACGGCCCAA CCCCACCCGC CAGCGAACTG CTCGATCACG    1320

GAGTACGTGG CTCGCGCGTT GGAAATGATC GGCAATACCG CGCCACAGGA CATCACCGGG    1380

CATCCGGCCA TGTCGATTCC GTGTGGCCTG CTGGACGGCC TGCCCGTCGG GCTGATGCTG    1440

GTCGCAAAAC ACTACGCCGA GGGCACGATT TACCAAGCGG CGGCGGCGTT TGAAGCCTCG    1500

GTGGACTGGC GCACGCTCTG A                                              1521
```

( 2 ) INFORMATION FOR SEQ ID NO:21:

( i ) SEQUENCE CHARACTERISTICS:
        ( A ) LENGTH: 384 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: P14K ( x i ) SEQUENCE DESCRIPTION: SEQ ID NO: 21:

```
ATGGCCCTGT GTTTGACGAG CCTTGGCAGT CCCAGGCGTT TGCCTTGGTG GTCAGCATGC      60

ACAAGGCCGG TCTCTTTCAG TGGAAAGACT GGGCCGAGAC CTTCACCGCC GAAATCGACG     120

CTTCCCCGCT CTGCCGGCGA AAGCGTCAAC GACACCTACT ACCGGCAATG GGTGTCGGCG     180

CTGGAAAAGT TGGTGGCGTC GCTGGGGCTT GTGACGGGTG GAGACGTCAA CTCGCGCGCA     240
```

```
CAGGAGTGGA  AACAGGCCCA  CCTCAACACC  CCACATGGGC  ACCCGATCCT  GCTGGCCCAT        300

GCGCTTTGCC  CGCCAGCGAT  CGACCCCAAG  CACAAGCACG  AGCCACAACG  CTCACCGATC        360

AAGGTCGTTG  CCGCAATGGC  TTGA                                                   384
```

( 2 ) INFORMATION FOR SEQ ID NO:22:

( i ) SEQUENCE CHARACTERISTICS:
        ( A ) LENGTH: 127 amino acids
        ( B ) TYPE: amino acid
        ( C ) STRANDEDNESS: unknown
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( B ) STRAIN: P14K ( x i ) SEQUENCE DESCRIPTION: SEQ ID NO: 22:

```
Met  Ala  Leu  Cys  Leu  Thr  Ser  Leu  Gly  Ser  Pro  Arg  Arg  Leu  Pro  Trp
  1             5                       10                      15

Trp  Ser  Ala  Cys  Thr  Arg  Pro  Val  Ser  Phe  Ser  Gly  Lys  Thr  Gly  Pro
             20                      25                      30

Arg  Pro  Ser  Pro  Pro  Lys  Ser  Thr  Leu  Pro  Arg  Ser  Ala  Gly  Glu  Ser
         35                      40                      45

Val  Asn  Asp  Thr  Tyr  Tyr  Arg  Gln  Trp  Val  Ser  Ala  Leu  Glu  Lys  Leu
     50                      55                      60

Val  Ala  Ser  Leu  Gly  Leu  Val  Thr  Gly  Gly  Asp  Val  Asn  Ser  Arg  Ala
 65                      70                      75                      80

Gln  Glu  Trp  Lys  Gln  Ala  His  Leu  Asn  Thr  Pro  His  Gly  His  Pro  Ile
                 85                      90                      95

Leu  Leu  Ala  His  Ala  Leu  Cys  Pro  Pro  Ala  Ile  Asp  Pro  Lys  His  Lys
                100                     105                     110

His  Glu  Pro  Gln  Arg  Ser  Pro  Ile  Lys  Val  Val  Ala  Ala  Met  Ala
             115                     120                     125
```

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 23:

```
GATGCGGCCA  TAGGCGAATT  C                                                      21
```

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 24:

```
ACCGCCACCG  ACTACCTGCA  G                                                      21
```

( 2 ) INFORMATION FOR SEQ ID NO:25:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 25:

```
GTCAGCCTGA GCAATCTGCA G                                                    21
```

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO: 26:

```
GAATTCGGAA AAAATCGTAC G                                                    21
```

( 2 ) INFORMATION FOR SEQ ID NO:27:

( i ) SEQUENCE CHARACTERISTICS:
        ( A ) LENGTH: 1401 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: AMIDASE ( x i ) SEQUENCE DESCRIPTION: SEQ ID NO: 27:

```
ATGAGTTCGC TAACCCGCCT CACCCTCGCG CAAGTTGCGC AGAAACTTAA GGCACGGGAA    60
GTCTCCGCCG TTGAAGTTCT GGACGCCTGT CTGACGCAGG TGCGCTCCAC CGAAAAACAG   120
ATCAGTGCGT ACGTGTGCGT GCTGGAGGAT CAGGCCCGTG CAGCAGCCCA CGCAACTGAC   180
GCCGACATCC GCGGGCGCTG GAAAGGCCCG CTGCATGGCG TGCCTGTAGC GGTCAAGGAC   240
TTATACGACA TCGCTGGCGT ACCCACCACG GCATCGTCGC CAGCGCACGA ATTGGACGCG   300
CAGCAAGACC CGGCTAGAGT CCGGCGCTTA CAAGACGCAG GTGCCGTTAT CCTTGGCAAG   360
ACCCATACGC ACGAATTCGC CTATGGCCGC ATCACTCCGA AGTCGCGCAA CCCCAGGGAC   420
CCGGGAAGAA CACCGGGTGG CTCCAGCGGC GGCTCGGCGG CCACGGTCGC AGCCTGCTGC   480
GTCTACTTGG CGACCGGCAC CGACACCGGT GGATCCGTTC GCATCCCTTC GTCGATGTGC   540
AACACCGTAG GCCTGAAGCA ACCTACGGTC GGCCGCGTGC ACGGTGCCGG TGTGAGTTCA   600
CTTTCCTGGA GCCTGGACCA TCCAGGCCCG ATCACGCGCA CCGTGGAAGA CACGGCGCTC   660
ATGCTTCAGG TGATGGCTGG CTTCGATCCA GCCGACCCGC GGTCGTTGGA TGAGCCGGTG   720
CCCAGCTATG CCGAAGGGCT CGGCCAAGGC GTGAAAGGCC TGCGCTGGGG TGTGCCGAAG   780
AACTACTTCT TCGACCGCGT GGACCCGGAA GTTGAAAGTG CGGTTCGTGC CGCCATCGAT   840
CAACTGAAAG AGCTGGGCGC CGAACTGGTG GAAGTCGAAG TGCCCATGGC CGAGCAGATC   900
```

-continued

```
ATCCCGGTGA   AGTTCGGGAT   CATGCTACCC   GAAGCCAGCG   CCTACCACCG   CACGATGCTG        960

CGCGAGTCAC   CCGAGCTCTA   CACCGCCGAT   GTCCGCATAC   TGCTGGAACT   CGGAGATCTA       1020

GTCACCGCCA   CCGACTACCT   GCAGGCGCAG   CGCGTCCGTA   CGCTGATGCA   GCGCGCGGTG       1080

GCCGAGATGT   ACCAGCGCAT   CGATGTGCTG   ATCGCACCCA   CACTGCCCAT   CCCGGCTGCT       1140

CGCAGCGGGG   AGGAGGTCCA   CACATGGCCG   GACGGCACGG   TAGAGGCGTT   GGTCATGGCC       1200

TATACGCGCT   TCACCTCGTT   CGGCAACGTG   ACAGGATTAC   CCACGCTGAA   CCTGCCCTGT       1260

GGTTTCTCCA   AGGATGGGTT   GCGATCGGCA   TGCAGATCAG   GCCGGCCGCT   GGACGAGAAG       1320

ACCCTGCTGC   GTGCTGGGCT   GGCCTACGAG   AAAGCCACGA   CCTGGCACCA   GCGTCATCCG       1380

GAACTGATCG   GAGCGGGCTG   A                                                       1401
```

(2) INFORMATION FOR SEQ ID NO:28:

(i) SEQUENCE CHARACTERISTICS:
        (A) LENGTH: 466 amino acids
        (B) TYPE: amino acid
        (C) STRANDEDNESS: unknown
        (D) TOPOLOGY: unknown (ii) MOLECULE TYPE: protein (iii) HYPOTHETICAL: NO (iv) ANTI-SENSE: NO (vi) ORIGINAL SOURCE:
        (B) STRAIN: AMIDASE (xi) SEQUENCE DESCRIPTION: SEQ ID NO: 28:

```
Met  Ser  Ser  Leu  Thr  Arg  Leu  Thr  Leu  Ala  Gln  Val  Ala  Gln  Lys  Leu
  1              5                        10                       15

Lys  Ala  Arg  Glu  Val  Ser  Ala  Val  Glu  Val  Leu  Asp  Ala  Cys  Leu  Thr
             20                       25                       30

Gln  Val  Arg  Ser  Thr  Glu  Lys  Gln  Ile  Ser  Ala  Tyr  Val  Cys  Val  Leu
                 35                       40                       45

Glu  Asp  Gln  Ala  Arg  Ala  Ala  Ala  His  Ala  Thr  Asp  Ala  Asp  Ile  Arg
         50                       55                       60

Gly  Arg  Trp  Lys  Gly  Pro  Leu  His  Gly  Val  Pro  Val  Ala  Val  Lys  Asp
 65                       70                       75                       80

Leu  Tyr  Asp  Ile  Ala  Gly  Val  Pro  Thr  Thr  Ala  Ser  Ser  Pro  Ala  His
                     85                       90                       95

Glu  Leu  Asp  Ala  Gln  Gln  Asp  Pro  Ala  Arg  Val  Arg  Arg  Leu  Gln  Asp
                100                      105                      110

Ala  Gly  Ala  Val  Ile  Leu  Gly  Lys  Thr  His  Thr  His  Glu  Phe  Ala  Tyr
            115                      120                      125

Gly  Arg  Ile  Thr  Pro  Lys  Ser  Arg  Asn  Pro  Arg  Asp  Pro  Gly  Arg  Thr
        130                      135                      140

Pro  Gly  Gly  Ser  Ser  Gly  Gly  Ser  Ala  Ala  Thr  Val  Ala  Ala  Cys  Cys
145                      150                      155                      160

Val  Tyr  Leu  Ala  Thr  Gly  Thr  Asp  Thr  Gly  Gly  Ser  Val  Arg  Ile  Pro
                    165                      170                      175

Ser  Ser  Met  Cys  Asn  Thr  Val  Gly  Leu  Lys  Gln  Pro  Thr  Val  Gly  Arg
                180                      185                      190

Val  His  Gly  Ala  Gly  Val  Ser  Ser  Leu  Ser  Trp  Ser  Leu  Asp  His  Pro
            195                      200                      205

Gly  Pro  Ile  Thr  Arg  Thr  Val  Glu  Asp  Thr  Ala  Leu  Met  Leu  Gln  Val
        210                      215                      220
```

| | | | | | | | | | | | | |
|---|---|---|---|---|---|---|---|---|---|---|---|---|
| Met 225 | Ala | Gly | Phe | Asp | Pro 230 | Ala | Asp | Pro | Arg | Ser 235 | Leu | Asp | Glu | Pro | Val 240 |
| Pro | Ser | Tyr | Ala | Glu 245 | Gly | Leu | Gly | Gln 250 | Val | Lys | Gly | Leu | Arg 255 | Trp |
| Gly | Val | Pro | Lys 260 | Asn | Tyr | Phe | Phe | Asp 265 | Arg | Val | Asp | Pro 270 | Glu | Val | Glu |
| Ser | Ala | Val 275 | Arg | Ala | Ala | Ile | Asp 280 | Gln | Leu | Lys | Glu 285 | Leu | Gly | Ala | Glu |
| Leu | Val 290 | Glu | Val | Glu | Val | Pro 295 | Met | Ala | Glu | Gln | Ile 300 | Ile | Pro | Val | Lys |
| Phe 305 | Gly | Ile | Met | Leu | Pro 310 | Glu | Ala | Ser | Ala | Tyr 315 | His | Arg | Thr | Met | Leu 320 |
| Arg | Glu | Ser | Pro | Glu 325 | Leu | Tyr | Thr | Ala | Asp 330 | Val | Arg | Ile | Leu | Leu 335 | Glu |
| Leu | Gly | Asp | Leu 340 | Val | Thr | Ala | Thr | Asp 345 | Tyr | Leu | Gln | Ala | Gln 350 | Arg | Val |
| Arg | Thr | Leu 355 | Met | Gln | Arg | Ala | Val 360 | Ala | Glu | Met | Tyr | Gln 365 | Arg | Ile | Asp |
| Val | Leu 370 | Ile | Ala | Pro | Thr | Leu 375 | Pro | Ile | Pro | Ala | Ala 380 | Arg | Ser | Gly | Glu |
| Glu 385 | Val | His | Thr | Trp | Pro 390 | Asp | Gly | Thr | Val | Glu 395 | Ala | Leu | Val | Met | Ala 400 |
| Tyr | Thr | Arg | Phe | Thr 405 | Ser | Phe | Gly | Asn | Val 410 | Thr | Gly | Leu | Pro | Thr 415 | Leu |
| Asn | Leu | Pro | Cys 420 | Gly | Phe | Ser | Lys | Asp 425 | Gly | Leu | Arg | Ser | Ala 430 | Cys | Arg |
| Ser | Gly | Arg 435 | Pro | Leu | Asp | Glu | Lys 440 | Thr | Leu | Leu | Arg | Ala 445 | Gly | Leu | Ala |
| Tyr | Glu 450 | Lys | Ala | Thr | Thr | Trp 455 | His | Gln | Arg | His | Pro 460 | Glu | Leu | Ile | Gly |
| Ala 465 | Gly |